United States Patent
Bebbington et al.

(10) Patent No.: US 8,398,972 B2
(45) Date of Patent: Mar. 19, 2013

(54) METHODS OF TREATING DEMENTIA USING A GM-CSF ANTAGONIST

(75) Inventors: Christopher R. Bebbington, South San Francisco, CA (US); Geoffrey T. Yarranton, South San Francisco, CA (US); Varghese Palath, South San Francisco, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 104 days.

(21) Appl. No.: 12/704,396

(22) Filed: Feb. 11, 2010

(65) Prior Publication Data

US 2010/0215650 A1   Aug. 26, 2010

Related U.S. Application Data

(63) Continuation-in-part of application No. 11/944,162, filed on Nov. 21, 2007.

(60) Provisional application No. 61/151,750, filed on Feb. 11, 2009, provisional application No. 60/860,780, filed on Nov. 21, 2006, provisional application No. 60/902,742, filed on Feb. 21, 2007.

(51) Int. Cl.
| | |
|---|---|
| A61K 39/395 | (2006.01) |
| A61K 39/00 | (2006.01) |
| A61K 38/18 | (2006.01) |
| A61P 25/28 | (2006.01) |
| C07K 14/475 | (2006.01) |

(52) U.S. Cl. ............... 424/130.1; 424/133.1; 424/141.1; 424/142.1; 424/158.1; 424/184.1; 514/17.8; 514/17.7; 514/17.3; 530/350

(58) Field of Classification Search .................. None
See application file for complete search history.

(56) References Cited

U.S. PATENT DOCUMENTS

| | | | |
|---|---|---|---|
| 5,475,087 A | 12/1995 | Seelig et al. | |
| 7,741,450 B2 * | 6/2010 | Sass et al. ................. | 530/388.23 |
| 7,931,899 B2 * | 4/2011 | Shafer et al. ............... | 424/133.1 |
| 2002/0010126 A1 | 1/2002 | Hamilton et al. | |
| 2004/0053365 A1 | 3/2004 | Renner et al. | |
| 2005/0255552 A1 | 11/2005 | Flynn et al. | |
| 2006/0134098 A1 | 6/2006 | Bebbington et al. | |
| 2007/0059280 A1 | 3/2007 | Devalaraja et al. | |
| 2008/0292641 A1 | 11/2008 | Sass et al. | |
| 2008/0305079 A1 | 12/2008 | Chen | |

FOREIGN PATENT DOCUMENTS

| | | |
|---|---|---|
| AU | 706462 B2 | 8/1997 |
| WO | WO 91/01330 A1 | 2/1991 |
| WO | WO 92/08474 A2 | 5/1992 |
| WO | WO 00/09561 A1 | 2/2000 |
| WO | WO 03/068920 A3 | 8/2003 |
| WO | WO 2006/111353 A2 | 10/2006 |
| WO | WO 2006/122797 A2 | 11/2006 |
| WO | WO 2007/092939 A2 | 8/2007 |
| WO | WO 2008/065321 A2 | 5/2008 |
| WO | WO 2008/141391 A1 | 11/2008 |

OTHER PUBLICATIONS

Grossman et al. Dementia: A Brief Review; The Mount Sinai Journal of Medicine vol. 73/7:985-992 (Nov. 2006).*
Valotassiou et al. (The role of nuclear medicine in vascular dementia; Vascular disease prevention vol. 3:353-357 (2006).*
Koutsilieri et al. Involvement of dopamine in the progression of AIDS dementia complex. Journal of Neural Transmission vol. 109:399-410 (2002).*
Castellani et al. Cerebral amyloid angiopathy: major contributor or decorative response to Alzheimer's disease pathogenesis, Neurobiology of Aging vol. 25:599-602 (2004).*
Moebius et al. Memantine hydrochloride: pharmacological and clinical profile, Drugs of Today. Abstract 40(8):685-695 (2004).*
Wada et al. Electroencephalograpic abnormalities in patients with presenile dementia of the Alzheimer Type: Quantitative Analysis at rest and during photic stimulation. Society of Biological Psychiatry vol. 41:217-225 (1997).*
Casset et al. A peptide mimetic of an anti-CD4 monoclonal antibody by rational design. Biochem. Biophys Res Comm vol. 307:198-205 (2003).*
MacCallum et al. Antibody-antigen interactions: Contact analysis and binding site topography J Mol Biol. vol. 262:732-745 (1996).*
Vajdos et al. Comprehensive Functional maps of the antigen-binding site of an anti-erbB2 antibody obtained with shotgun scanning mutagenesis. J Mol Biol. vol. 320(2):415-428 (2002).*
Bose and Sinha. Problems in using statistical analysis of replacement and silent mutations in antibody genes for determining antigen-driven affinity selection; Immunology vol. 116:172-183 (2005).*
Solomon, B. Generation of anti-B-amyloid antibodies via phage display technology towards Alzheimer's disease vaccination. Vaccine, vol. 23:2327-2330 (Feb. 2005).*
Hartman et al. Treatment with an Amyloid-B Antibody Ameliorates Plaque Load, Learning Deficits, and Hippocampal Long-Term Potentiation in a Mouse Model of Alzheimer's Disease. The Journal of Neuroscience, vol. 25(26):6213-6220 (Jun. 2005).*
Thakker et al. Intracerebroventricular amyloid-B antibodies reduce cerebral amyloid angiopathy and associated micro-hemorrhages in aged Tg2576 mice. PNAS, vol. 106/11:4501-4506 (Mar. 2009).*
Greig et al. An Overview of Phenserine Tartrate, A Novel Acetylcholinesterase Inhibitor for the Treatment of Alzheimer's Disease. Current Alzheimer Research, vol. 2 Issue 3, p. 281-290 (Jul. 2005).*

(Continued)

Primary Examiner — Elizabeth C Kemmerer
Assistant Examiner — Regina M Deberry
(74) Attorney, Agent, or Firm — Kilpatrick Townsend & Stockton LLP

(57) ABSTRACT

The invention is based on the discovery that GM-CSF antagonists can be used for the treatment of a patient that has Alzheimer's disease or vascular dementia, or is at risk for developing Alzheimer's disease. Accordingly, the invention provides methods of administering a GM-CSF antagonist, e.g., a GM-CSF antibody and pharmaceutical compositions comprising such antagonists.

30 Claims, 5 Drawing Sheets

OTHER PUBLICATIONS

Moebius et al. Functional improvement from treatment with the NMDA antagonist memantine: Results of a 28-week, randomized, placebo-controlled study in advanced Alzheimer's disease. European Neuropsychopharmacology vol. 13, No. Suppl 4, Abstract p. S388 Meeting Info: 7$^{th}$ Congress of the European Federation of Neurological Societies (Sep. 2003).*

Istrin et al. Intravenous Immunoglobulin Enhances the Clearance of Fibrillar Amyloid-b Peptide. Journal of Neuroscience Research 84:434-443 (2006).*

Abdelaziz, M.M. et al.; "The Effect of Conditioned Medium from Cultured Human Bronchial Epithelial Cells on Eosinophil and Neutrophil Chemotaxis and Adherence in Vitro"; 1995, *Am. J. Respir. Cell Mol. Bio.*, vol. 13, pp. 728-737.

Adams, Jared R. et al.; "When the Risk of Febrile Neutropenia is 20%, Prophylactic Colony-Stimulating Factor Use Is Clinically Effective, but Is It Cost-Effective?"; 2006, *Journal of Clinical Oncology*, vol. 24, No. 19, pp. 2975-2977.

Aglietta, Massimo et al.; "Short-term Administration of Granulocyte-Macrophage Colony Stimulating Factor Decreases Hematopoietic Toxicity of Cytostatic Drugs"; 1993, *Cancer*, vol. 72, pp. 2970-2973.

Alvaro-Gracia, Jose M. et al.; "Cytokines in Chronic Inflammatory Arthritis"; 1989, *J. Exp. Med.*, vol. 170, pp. 865-875.

Anwar, A.R.F. et al.; "Adhesion to Fibronectin Prolongs Eosinophil Survival"; 1993, *J. Exp. Med.*, vol. 177, pp. 839-843.

Brach, Marion A. et al.; "Prolongation of Survival of Human Polymorphonuclear Neutrophils by Granulocyte-Macrophage Colony-Stimulating Factor Is Caused by Inhibition of Programmed Cell Death"; 1992, *Blood*, vol. 80, No. 11, pp. 2920-2924.

Campbell, Ian K. et al.; "Granulocyte-macrophage colony stimulating factor exacerbates collagen induced arthritis in mice"; 1997, *Ann. Rheum. Dis.*, vol. 56, pp. 364-368.

Campbell, Ian K. et al.; "Protection from Collagen-Induced Arthritis in Granulocyte-Macrophage Colony-Stimulating Factor-Deficient Mice"; 1998, *The Journal of Immunology*, vol. 161, pp. 3639-3644.

Campbell, Ian K. et al.; "The colony-stimulating factors and collagen-induced arthritis: exacerbation of disease by M-CSF and G-CSF and requirement for endogenous M-CSF"; 2000, *Journal of Leukocyte Biology*, vol. 68, pp. 144-150.

Chen, Thomas T. et al.; "Induction of Autoantibody Responses to GM-CSF by Hyperimmunization with an Id-GM-CSF Fusion Protein"; 1994, *Journal of Immunology*, pp. 3105-3117.

Cook, Andrew D. et al.; "Blockade of collagen-induced arthritis post-onset by antibody to granulocyte-macrophage colony-stimulating factor (GM-CSF): requirement for GM-CSF in the effector phase of disease"; 2001, *Arthritis Res.*, vol. 3, pp. 293-298.

Cook, Andrew D. et al.; "Stimulus-Dependent Requirement for Granulocyte-Macrophage Colony-Stimulating Factor in Inflammation"; 2004, 994, *Journal of Immunology*, pp. 4643-4651.

Cronstein, Bruce N.; "Low-Dose Methotrexate: A Mainstay in the Treatment of Rheumatoid Arthritis"; 2005, *Pharmacological Reviews*, vol. 57, No. 2, pp. 163-172.

Davies, Robert J. et al.; "New Insights Into the Understanding of Asthma"; 1997, *Chest*, vol. 111, pp. 2-10.

Dempsey, Peter J. et al.; "Monoclonal Antibodies that Recognize Human Granulocyte-Macrophage Colony-Stimulating Factor and Neutralize Its Bioactivity in Vitro"; 1990, *Hybridoma*, vol. 9, No. 6, pp. 545-558.

DeNichilo, Mark O. et al.; "Granulocyte-Macrophage Colony-stimulating Factor Is a Stimulant of Platelet-activating Factor and Superoxide Anion Generation by Human Neutrophils"; 1991, *The Journal of Biological Chemistry*, vol. 266, No. 8, pp. 4896-4902.

Edwards, Jonathan C.W. et al.; "Efficacy of β-Cell-Targeted Therapy with Rituximab in Patients with Rheumatoid Arthritis"; 2004, *New England Journal of Medicine*, vol. 350, pp. 2572-2581.

Fleischmann, Roy et al.; "Anakinra: an inhibitor of IL-1 for the treatment of rheumatoid arthritis"; 2004, *Expert Opin. Biol. Ther.*, vol. 4, No. 8, pp. 1333-1344.

Giasuddin, Abu Sayed M. et al.; "Views for Future Development Cytokines in Health and Disease: Implications for Clinical Medicine"; 1996, *Journal of Islamic Academy of Sciences*, vol. 9, No. 3, pp. 67-74.

Gibson, Peter G. et al.; "Epidemiological Association of Airway Inflammation with Asthma Symptoms and Airway Hyperresponsiveness in Childhood"; 1998, *Am. J. Respir. Crit. Care Med.*, vol. 158, pp. 36-41.

Gong, Kaizheng et al.; "The nonspecific anti-inflammatory therapy with methotrexate for patients with chronic heart failure"; 2006, *American Heart Journal*, vol. 151, No. 1, pp. 62-68.

Hallsworth, Matthew P. et al.; "Selective enhancement of GM-CSF, TNF-α, IL-1β and IL-8 production by monocytes and macrophages of asthmatic subjects"; 1994, *Eur. Respir. J.*, vol. 7, pp. 1096-1102.

Hallsworth, Matthew P. et al.; "Cultured Human Airway Smooth Muscle Cells Stimulated by Interleukin-1β enhanced Eosinophil Survival"; 1998, *Am. J. Respir., Cell Mol. Biol.*, vol. 19, pp. 910-919.

Hamilton, John A.; "GM-CSF in inflammation and autoimmunity"; 2002, *Trends in Immunology*, vol. 23, No. 8, pp. 403-408.

Hemachandra, Reddy P. et al.; "Granulocyte-macrophage colony-stimulating factor antibody suppresses microglial activity: implications for anti-inflammatory effects in Alzheimer's disease and multiple sclerosis"; 2009, *Journal of Neurochemistry*, vol. 111, No. 6, pp. 1514-1528.

Hercus, Timothy R. et al.; "Specific human granulocyte-macrophage colony-stimulating factor antagonists"; 1994, *Proceedings of the National Academy of Sciences*, vol. 91, pp. 5838-5842.

Hitter-Paier, Birgit et al.; "The ACAT inhibitor CP-113, 818 markedly reduces amyloid pathology in a mouse model of Alzheimer's disease"; 2004, *Neuron*, vol. 44, No. 2, pp. 227-238.

Krinner, Eva-Maria et al.; "A human monoclonal IgG1 potently neutralizing the pro-inflammatory cytokine GM-CSF"; 2007, *Molecular Immunology*, vol. 44, pp. 916-925.

Lei, X.F. et al.; "Compartmentalized transgene expression of granulocyte-macrophage colony-stimulating factor (GM-CSF) in mouse lung enhances allergic airways inflammation"; 1998, *Clin. Exp. Immunol.*, vol. 113, pp. 157-165.

Leizer, Tali et al.; "Cytokine Regulation of Colony-Stimulating Factor Production in Cultured Human Synovial Fobroblasts: I. Induction of GM-CSF and G-CSF Production by Interleukin-1 and Tumor Necrosis Factor"; 1990, *Blood*, vol. 76, No. 10, pp. 1989-1996.

Li, Jian et al.; "Human antibodies for immunotherapy development generated via a human B cell hybridoma technology"; 2006, *Proceedings of the National Academy of Sciences*, vol. 103, No. 10, pp. 3557-3562.

Manczak, Maria et al.; "Neutralization of granulocyte macrophage colony-stimulating factor decreases amyloid beta 1-42 and suppresses microglial activity in a transgenic mouse model of Alzheimer's disease"; 2009, *Human Molecular Genetics*, vol. 18, No. 20, pp. 3876-3893.

Mattoli, S. et al.; "Expression of the potent inflammatory cytokines, GM-CSF, IL6, and IL8, in bronchial epithelial cells of asthmatic patients"; 1992, *Chest*, vol. 101, pp. 27-29.

McQualter, Jonathan L. et al.; "Granulocyte Macrophage Colony-stimulating Factor: A New Putative Therapeutic Target in Multiple Sclerosis"; 2001, *J. Exp. Med.*, vol. 194, No. 7, pp. 873-881.

Nakajima, Yasuyuki; "An Essential Role of Granulocyte Macrophage-Colony Stimulating Factor (GM-CSF) in Airway Hyperresponsiveness"; 1999, *Teikyo Medical Journal*, vol. 22, No. 2, pp. 147-154.

Nakamura, Yoichi et al.; "Upregulatory Effects of Interleukin-4 and Interleukin-13 but not Interlukin-10 on Granulocyte/macrophage Colony-stimulating Factor Production by Human Bronchial Epithelial Cells"; 1996, *Am. J. Respir. Cell Mol. Biol.*, Nol. 15, pp. 680-687.

Ohkawara, Yuichi et al.; "CD40 Expression by Human Peripheral Blood Eosinophils"; 1996, *J. Clin. Invest.*, vol. 97, No. 7, pp. 1761-1766.

Ohta, Ken et al.; "Diesel exhaust particulate induces airway hyperresponsiveness in a murine model: Essential role of GM-CSF"; 1999, *The Journal of Allergy and Clinical Immunology*, vol. 104, No. 5, pp. 1024-1030.

Olsen, Nancy J. et al.; "New Drugs for Rheumatoid Arthritis"; 2004, *New England Journal of Medicine*, vol. 350, pp. 2167-2179.
Park, C.S. et al.; "Granulocyte macrophage colony-stimulating factor is the main cytokine enhancing survival of eosinophils in asthmatic airways"; 1998, *Eur. Respir. J.*, vol. 12, pp. 872-878.
Puljic, Ruzica et al.; "Lipopolysaccharide-induced lung inflammation is inhibited by neutralization of GM-CSF"; 2007, *European Journal of Pharmacology*, vol. 557, pp. 230-235.
Riksen, N.P. et al.; "Methotrexate modulates the kinetics of adenosine in humans in vivo"; 2006, *Ann. Rheum. Dis.*, vol. 65, pp. 465-470.
Robertson, Fredika M. et al.; "Granulocyte-macrophage colony stimulating factor gene expression and function during tumor promotion"; 1994, *Carcinogenesis*, vol. 15, No. 5, pp. 1017-1029.
Sekiyama, Naho et al.; "Modulation of Neutrophil Apoptosis in Rheumatoid Arthritis"; 1996, *Kitasato Med.*, vol. 26, pp. 275-281.
Sosin, Michael et al.; "Low dose methotrexate and bone marrow suppression"; 2003, *BMJ*, vol. 326, pp. 266-267.
Spoelstra, Fokje M. et al.; Changes in CD11b and L-selectin Expression on Eosinophils Are Mediated by Human Lung Fibroblasts in Vitro; 1998, *Am. J. Respir. Crit. Care Med.*, vol. 158, pp. 769-777.
Stanley, Edouard et al.; "Granulocyte / macrophage colony-stimulating factor-deficient mice show no major perturbation of hematopoiesis but develop a characteristic pulmonary pathology"; *Proceedings of the National Academy of Sciences*, vol. 91, pp. 5592-5596.
Svenson, Morten et al.; "Antibody to Granulocyte-Macrophage Colony-Stimulating Factor Is a Dominant Anti-Cytokine Activity in Human IgG Preparations"; 1998, *Blood*, vol. 91, No. 6, pp. 2054-2061.
Takahashi, Masafumi et al.; "Human Monocyte-Endothelial Cell Interaction Induces Synthesis of Granulocyte-Macrophage Colony-Stimulating Factor"; 1993, *Circulation*, vol. 93, No. 6, pp. 1185-1193.
Takanaski, Shingo et al.; "Interleukin 10 Inhibits Lipopolysaccharide-induced Survival and Cytokine Production by Human Peripheral Blood Eosinophils"; 1994, *J. Exp. Med.*, vol. 180, pp. 711-715.
Takimoto, Chris H.; "New Antifolates: Pharmacology and Clinical Applications"; 1996, *The Oncologist*, vol. 1, pp. 68-81.
Tarkowski, E. et al.; "local and systemic GM-CSF increase in Alzheimer's disease and vascular dementia"; 2001, *Acta Neurologica Scandinavica*, vol. 103, No. 3, pp. 166-174.
Tiegs, G. et al.; "Potentiation by Granulocyte Macrophage Colony-stimulating Factor of Lipopolysaccharide Toxicity in Mice"; 1994, *J. Clin. Invest.*, vol. 93, pp. 2616-2622.
Tony, J.C.; "Granulocyte-macrophage colony stimulating fctor and bronchial asthma—A hypothesis for novel therapeutic options"; 1995, *Letters to the Editor*, pp. 713.
Vancheri, C. et al.; "Human Lung Firbroblast-derived Granulocyte-Macrophage Colony Stimulating Factor (GM-CSF) Mediates Eosinophil"; 1989, *Am. J. Repir. Cell Mol. Biol.*, vol. 1, pp. 289-295.
Vasunia, Kersi B. et al.; "Granulocyte-macrophage colony-stimulating factor (GM-CSF) is expressed in mouse skin in response t tumor-promoting agents and modulates dermal inflammation and epidermal dark cell numbers"; 1994, *Carcinogenesis*, vol. 15, No. 4, pp. 653-660.
Volmar, C.H. et al.; "The granulocyte macrophage colony stimulating factor (GM-CSF) regulates amyloid beta (Abeta) production"; 2008, *Cytokine, Academic Press Ltd.*, vol. 42, No. 3, pp. 336-344.
Whittle, S.L. et al.; "Folate supplementation and methotrexate treatment in rheumatoid arthritis: a review"; 2004, *Rheumatology*, vol. 43, pp. 267-271.
Williams, William V.; "GM-CSF Antagonists"; 2001, *Prog. Respir. Res.*, vol. 31, pp. 251-255.
Xing, Zhou et al.; "Human Upper Airway Structural Cell-derived Cytokines Support Human Peripheral Blood Monocyte Survival: A Potential Mechanism for Monocyte/Macrophage Accumulation in the Tissue"; 1992, *Am. J. Respir. Cell Mol. Biol.*, vol. 6, pp. 212-218.
Xing, Zhou et al.; "Transfer of Granulocyte-Macrophage Colony-stimulating Factor Gene to Rat Lung Induces Eosinophilia, Monocytosis, and Fibrotic Reactions"; 1996, *J. Clin. Invest.*, vol. 97, No. 4, pp. 1102-1110.
Franzen, Rachelle et al.; "Nervous system injury: focus on the inflammatory cytokine 'granulocyte-macrophage colony stimulating factor"; 2004, *Neuroscience*, vol. 361, pp. 76-78.
Jekabsone, Aiste et al.; "Fibrillar beta-amyloid peptide A$\beta_{1-40}$ activities microglial proliferation via stimulating TNF-$\alpha$ release and $H_2O_2$ derived from NADPH oxidase: a cell culture study"; 2006, *Journal of Neuroinflammation*, vol. 3, No. 4, 13 pages.
Okello, A. et al.; "Microglial activation and amyloid deposition in mild cognitive impairment: A PET study"; 2009, *Neurology*, vol. 72, pp. 56-72.

\* cited by examiner

FIGURE 1

```
VH1 1-02    QVQLVQSGAEVKKPGASVKVSCKASGYTFTGYYMHWVRQAPGQGLEWMGWINPNSGGTNYAQKFQGRVIMTRDTSISTAYMELSRLRSDDTAVYYCAR----------------------------------
VH#1        QVQLVQSGAEVKKPGASVKVSCKASGYTFTGYYMHWVRQAPGQGLEWMGWINPNSGGTNYAQKFQGRVIMTRDTSISTAYMELSRLRSDDTAVYYCVRRDRFPYIFDYWGQGTLVTVSS

VH1 1-03    QVQLVQSGAEVKKPGASVKVSCKASGYTFTSYAMHWVRQAPGQRLEWMGWINAGNGNTKYSQKFQGRVTITRDTSASTAYMELSLRSEDTAVYYCAR----------------------------------
VH#2        QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCARRDRFPYYFDYWGQGTLVTVSS
VH#3        QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCARRQRFPYYFDYWGQGTLVTVSS
VH#4        QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCVRRQRFPYYFDYWGQGTLVTVSS
VH#5        QVQLVQSGAEVKKPGASVKVSCKASGYSFTNYYIHWVRQAPGQRLEWMGWINAGNGNTKYSQKFQGRVTITRDTSASTAYMELSLRSEDTAVYYCVRRQRFPYYFDYWGQGTLVTVSS

VKIII A27   EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP-----------
VK#1        EIVLTQSPATLSVSPGERATLSCRASQSVGTN-VAWYQQKPGQAPRVLIYSTSSRATGITDRFSGSGSGTDFTLTISRLEPEDFAVYYCQQFNRSPLTFGGGTKVEIK
VK#2        EIVLTQSPATLSVSPGERATLSCRASQSVGTN-VAWYQQKPGQAPRVLIYSTSSRATGITDRFSGSGSGTDFTLTISRLEPEDFAVYYCQQFNKSPLTFGGGTKVEIK
VK#3        EIVLTQSPATLSVSPGERATLSCRASQSIGSN-LAWYQQKPGQAPRVLIYSTSSRATGITDRFSGSGSGTDFTLTISRLEPEDFAVYYCQQFNRSPLTFGGGTKVEIK
VK#4        EIVLTQSPATLSVSPGERATLSCRASQSIGSN-LAWYQQKPGQAPRVLIYSTSSRATGITDRFSGSGSGTDFTLTISRLEPEDFAVYYCQQFNKSPLTFGGGTKVEIK
```

| Fab | Vh | Vk | Dissociation rate for binding to GM-CSF determined by surface plasmon resonance analysis (s$^{-1}$) |
|---|---|---|---|
| FB42-8 | #2 | #3 | 1.36 x 10$^{-4}$ |
| FB44-5 | #1 | #3 | 8.0 x 10$^{-5}$ |
| FB77-2 | #3 | #1 | 5.57 x 10$^{-5}$ |
| FB92-1 | #4 | #4 | 3.84 x 10$^{-5}$ |
| FB94-1 | #4 | #2 | 3.12 x 10$^{-5}$ |
| FB104-1 | #5 | #1 | 3.57 x 10$^{-5}$ |
| FB106-1 | #5 | #2 | 5.4 x 10$^{-5}$ |

Figure 2
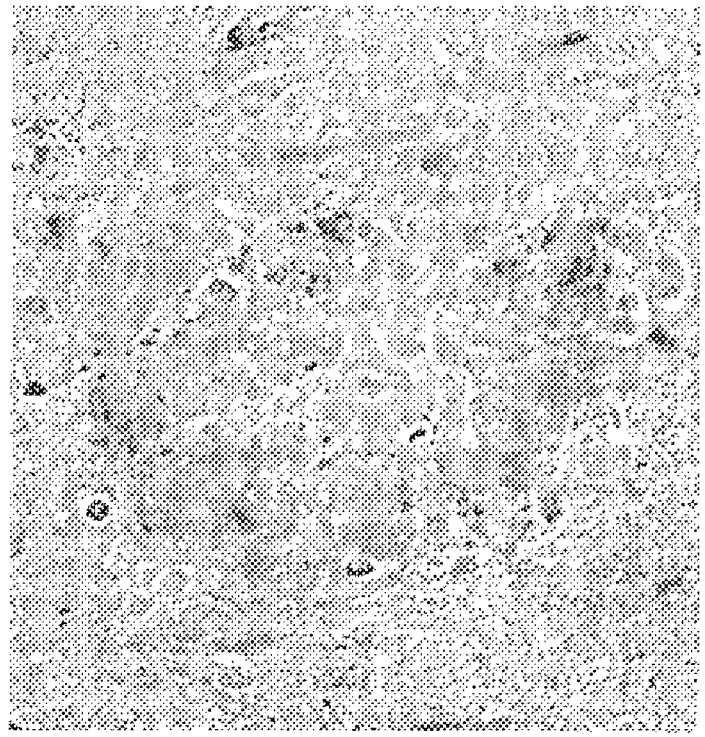
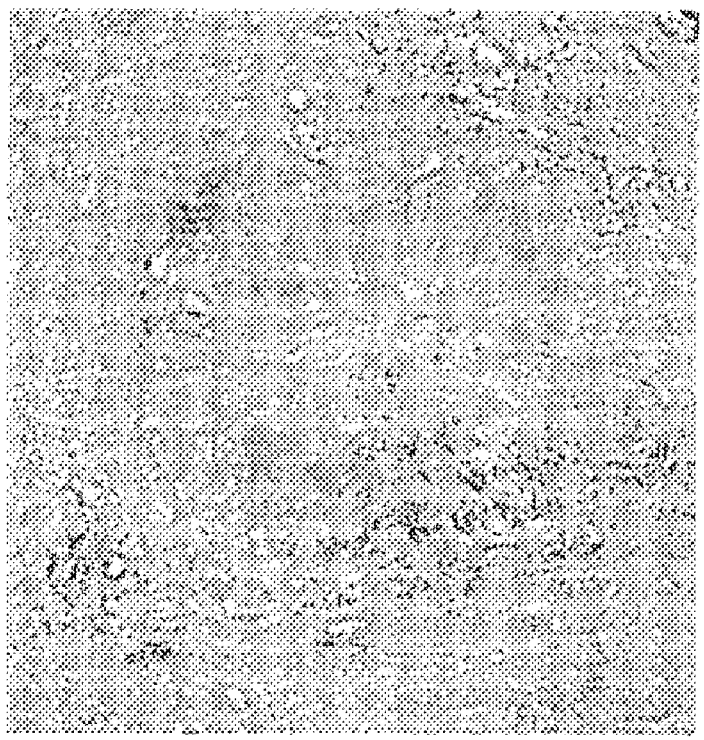

Figure 3
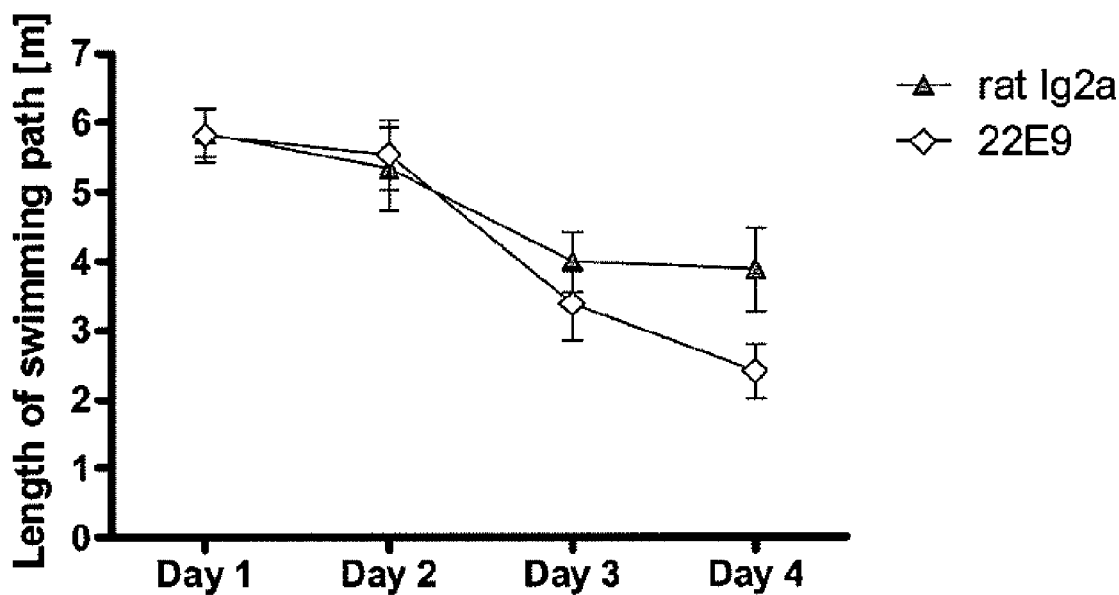
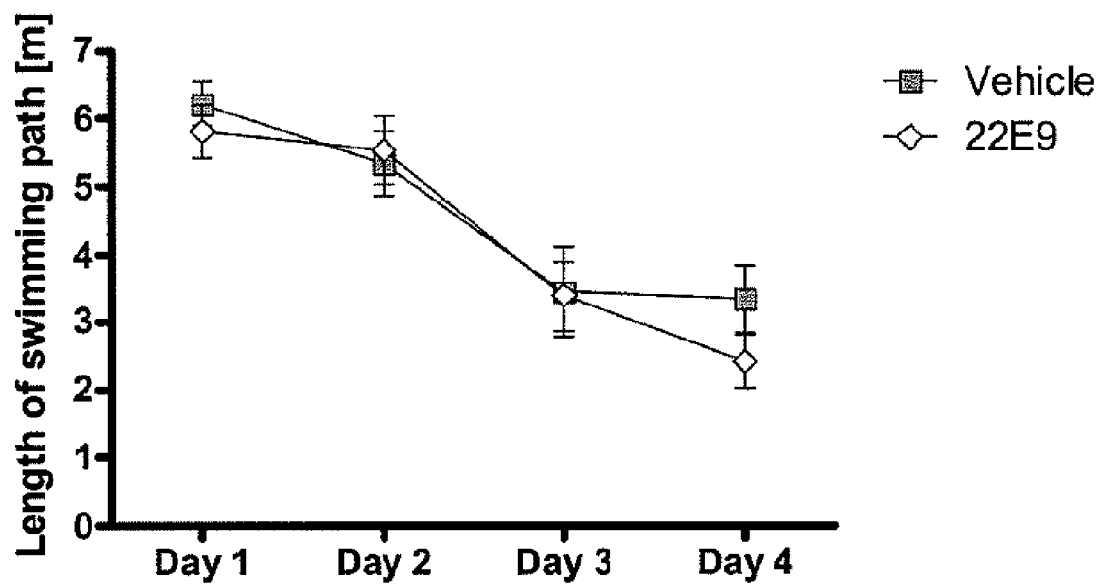

METHODS OF TREATING DEMENTIA USING A GM-CSF ANTAGONIST

CROSS-REFERENCE TO RELATED APPLICATIONS

This application claims benefit of U.S. provisional application No. 61/151,750, filed Feb. 11, 2009; and is a continuation-in-part of U.S. patent application Ser. No. 11/944,162, filed Nov. 21, 2007, which claims benefit of U.S. provisional application No. 60/860,780, filed Nov. 21, 2006; and U.S. provisional application No. 60/902,742, filed Feb. 21, 2007. This application is also related to U.S. provisional application No. 61/048,522, filed Apr. 28, 2008. Each of the noted applications is herein incorporated by reference.

BACKGROUND OF THE INVENTION

Granulocyte-macrophage colony-stimulating factor (GM-CSF) is a cytokine that plays a role in the inflammatory response and has been reported to be involved in mediating aspects of a number of chronic inflammatory diseases, including rheumatoid arthritis, psoriasis, ankylosing spondylitis, juvenile idiopathic arthritic, and systemic lupus erythematosus. Elevated levels of GM-CSF have been also observed in the cerebrospinal fluid and sera of patients with Alzheimer's disease and vascular dementia (Tarkowski et al. *Acta Neurol. Scand* 103:166-174, 2001); however a role of GM-CSF in the pathology of dementia has not been identified. This invention is based, in part, on the discovery that a GM-CSF antagonist can be used for the treatment of dementia, or a patient at risk of developing dementia.

BRIEF SUMMARY OF THE INVENTION

The present invention provides methods to treat a patient suffering from dementia, such as Alzheimer's disease, vascular dementia, cerebral amyloid angiopathy (CAA); or a patient at risk of developing dementia such as Alzheimer's disease, vascular dementia, or CAA, e.g., where the patient is diagnosed with mild cognitive impairment or a has a family history of familial Alzheimer's disease. The methods of the invention comprise administering a GM-CSF antagonist to the patient in a therapeutically effective amount, which at least partially arrests symptoms and/or slows the progression or onset of the disease. In typical embodiments, the GM-CSF antagonist is a recombinant protein. A patient treated as described herein may be diagnosed with one of the disease conditions (Alzheimer's, vascular dementia, or CAA), or may be diagnosed with a combination of these conditions. Thus, for example, a patient treated in accordance with the invention may have CAA as well as vascular dementia, or CAA as well as Alzheimer's, or vascular dementia and Alzheimer's disease, or all three of the conditions. Treatment with the GM-CSF antagonist can be performed alone, or in conjunction with other therapies, such as treatment with an anti-beta-amyloid antibody, a beta-amyloid vaccine, an acetylcholinesterase inhibitor, an NMDA receptor antagonist, or IVIG. In some embodiments, the invention provides a method of administering a GM-CSF antagonist, e.g., an antibody, to a patient that has dementia, such as Alzheimer's disease, with the proviso that the GM-CSF antagonist is not human IVIG.

The invention additionally provides a GM-CSF antagonist as described herein for use in treating dementia, or risk or dementia as described in the preceding paragraph. The methods, uses and pharmaceutical compositions for treating a patient in accordance with the invention can employ any GM-CSF antagonist described herein including any of the following antagonists:

In some embodiments of the invention, the GM-CSF antagonist is recombinantly produced, e.g., a recombinant monoclonal antibody. In other embodiments, the GM-CSF antagonist, e.g., purified anti-GM-CSF from human plasma, is purified from a natural source. In some embodiments, the GM-CSF antagonist is a recombinant anti-GM-CSF antibody, an anti-GM-CSF receptor antibody; a GM-CSF analog, e.g., such as a peptide analog, a soluble GM-CSF receptor; a cytochrome b562 antibody mimetic; an adnectin, a lipocalin scaffold antibody mimetic; a calixarene antibody mimetic, or an antibody-like binding peptidomimetic.

In many embodiments, the GM-CSF antagonist is an antibody to GM-CSF, i.e., an anti-GM-CSF antibody. In typical embodiments, the anti-GM-CSF antibody is a recombinant antibody. In various embodiments, the antibody can be a polyclonal antibody, a monoclonal antibody, or an antibody such as a nanobody or a camelid antibody. In some embodiments, the antibody is an antibody fragment, such as a Fab, a Fab', a F(ab')$_2$, a scFv, or a domain antibody (dAB). The antibody can also be modified, e.g., to enhance stability. For example, in some embodiments, the antibody is conjugated to polyethylene glycol.

In some embodiments, the antibody has an affinity of about 100 pM to about 10 nM, e.g., from about 100 pM, about 200 pM, about 300 pM, about 400 pM, about 500 pM, about 600 pM, about 700 pM, about 800 pM, about 900 pM, or about 1 nM to about 10 nM. In further embodiments, the antibody has an affinity of about 1 pM to about 100 pM, e.g., an affinity of about 1 pM, about 5 pM, about 10 pM, about 15 pM, about 20 pM, about 25 pM, about 30 pM, about 40 pM, about 50 pM, about 60 pM, about 70 pM, about 80 pM, or about 90 pM to about 100 pM. In some embodiments, the antibody has an affinity of from about 10 to about 30 pM. In some embodiments, the antibody has from 10-1000 fM affinity.

In some embodiments, the antibody is a neutralizing antibody. In further embodiments, the antibody is a recombinant or chimeric antibody. In some embodiments, the antibody is a human antibody. In some embodiments, the antibody comprises a human variable region. In some embodiments, the antibody comprises a human light chain constant region. In some embodiments, the antibody comprises a human heavy chain constant region, such as a gamma chain.

In further embodiments, the antibody competes for binding to the same epitope as a chimeric 19/2 antibody, which is a chimeric antibody obtained from the mouse monoclonal antibody LMM102. The antibody can, e.g., comprise the $V_H$ and $V_L$ regions of chimeric 19/2. The antibody can also comprise a human heavy chain constant region such as a gamma region. In some embodiments, the antibody comprises the CDR1, CDR2, and CDR3 of the $V_H$ region of chimeric 19/2. In further embodiments, the antibody comprises the CDR1, CDR2, and CDR3 of the $V_L$ region of chimeric 19/2. In additional embodiments, the antibody comprises the CDR1, CDR2, and CDR3 of the $V_H$ and $V_L$ regions of a chimeric 19/2 antibody. In some embodiments, the antibody comprises the $V_H$ region CDR3 and $V_L$ region CDR3 of chimeric 19/2.

In some embodiments, an anti-GM-CSF antibody for use in the invention comprises a $V_H$ region that has a CDR3 binding specificity determinant RQRFPY (SEQ ID NO:1) or RDRFPY (SEQ ID NO:2), a J segment, and a V-segment, wherein the J-segment comprises at least 95% identity to human JH4 (YFDYWGQGTLVTVSS; SEQ ID NO:3) and the V-segment comprises at least 90% identity to a human germ line VH1 1-02 or VH1 1-03 sequence. In some embodiments, the antibody comprise a $V_H$ region that comprises a CDR3 binding specificity determinant comprising RQRFPY (SEQ ID NO:1). In some embodiments, the J segment comprises YFDYWGQGTLVTVSS (SEQ ID NO:3). In some embodiments, the anti-GM-CSF antibody has a CDR3 that comprises RQRFPYYFDY (SEQ ID NO:4) or RDRFPYY-FDY (SEQ ID NO:5). In some embodiments the $V_H$ region CDR1 is a human germline VH1 CDR1; the $V_H$ region CDR2 is a human germline VH1 CDR2; or both $V_H$ region the CDR1 and CDR2 are human germline VH1. In some embodiments, the antibody comprises a $V_H$ CDR1, or a $V_H$ CDR2, or both a $V_H$ CDR1 and a $V_H$ CDR2 as shown in a $V_H$ region set forth in FIG. 1. In some embodiments, the V-segment sequence has a $V_H$ V segment sequence shown in FIG. 1. In further embodiments, the $V_H$ has the sequence of VH#1, VH#2, VH#3, VH#4, or VH#5 set forth in FIG. 1.

In some embodiments, an anti-GM-CSF antibody of the invention, e.g., an anti-GM-CSF antibody having $V_H$ region as described herein, comprises a $V_L$ region that comprises a CDR3 binding specificity determinant FNK or FNR. In some embodiments, the antibody comprises a human germline JK4 region. In some embodiments, the $V_L$ region CDR3 comprises QQFN(K/R)SPLT (SEQ ID NO:6). In some embodiments, the $V_L$ region comprises a CDR1, or a CDR2, or both a CDR1 and CDR2 of a sequence $V_L$ region shown in FIG. 1. In some embodiments, the $V_L$ region comprises a V segment that has at least 95% identity to the VKIIIA27 V-segment sequence as shown in FIG. 1. In some embodiments, the $V_L$ region has the sequence of VK#1, VK#2, VK#3, or VK#4 set forth in FIG. 1.

In some embodiments, an anti-GM-CSF antibody for use in the invention has a half-life of about 7 to about 25 days.

In some embodiments of the methods of the invention, the GM-CSF antagonist, e.g., an anti-GMCSF antibody, is administered by injection or by infusion. For example, the GM-CSF antagonist can be administered intravenously over a period between about 15 minutes and about 2 hours.

In other embodiments, the GM-CSF antagonist is administered subcutaneously by bolus injection.

In further embodiments, the GM-CSF antagonist is administered by intranasal administration, perispinal administration, intrathecal administration, or subcutaneous administration.

A GM-CSF antibody can, for example, be administered at a dose between about 1 mg/kg of body weight and about 10 mg/kg of body weight.

In some embodiments, treatment with the GM-CSF antagonist comprises a second administration of the GM-CSF antagonist.

The invention also provides a method of treating a patient having Alzheimer's disease, vascular dementia, or CAA, or who is at risk for developing Alzheimer's disease or vascular dementia, the method comprising administering an anti-GM-CSF antibody as described herein to the patient in a therapeutically effective amount.

BRIEF DESCRIPTION OF THE DRAWINGS

FIG. 1 provides exemplary $V_H$ (SEQ ID NOS:8 and 10-13) and $V_L$ (SEQ ID NOS:15-18) sequences of anti-GM-CSF antibodies. VH1 1-02=SEQ ID NO:7; VH1 1-03=SEQ ID NO:9; VKIII A27=SEQ ID NO:14.

FIG. 2. Uptake of 22E9 into the hippocampus region of the brain of a hAPP751-SL transgenic mouse. The mouse was administered 22E9 antibody (rat anti-mouse anti-GM-CSF neutralizing antibody) 48 hours prior to sacrifice and sectioning of the brain. 22E9 is detected using anti-rat IgG specific antibody. The figure shows 22E9 antibody uptake associated with amyloid plaques in the hippocampus region of the brain after A) intravenous (i.v.) administration or B) intranasal (i.n.) administration FIG. 3. Performance of anti-GM-CSF antibody 22E9 treated and control mice in the Morris Water Maze beginning 44 days after treatment initiation. Mean swimming path length is shown (+standard error). * Difference between rat IgG2a treated and 22E9 treated mice is statistically significant.

DETAILED DESCRIPTION OF THE INVENTION

Figure 4:
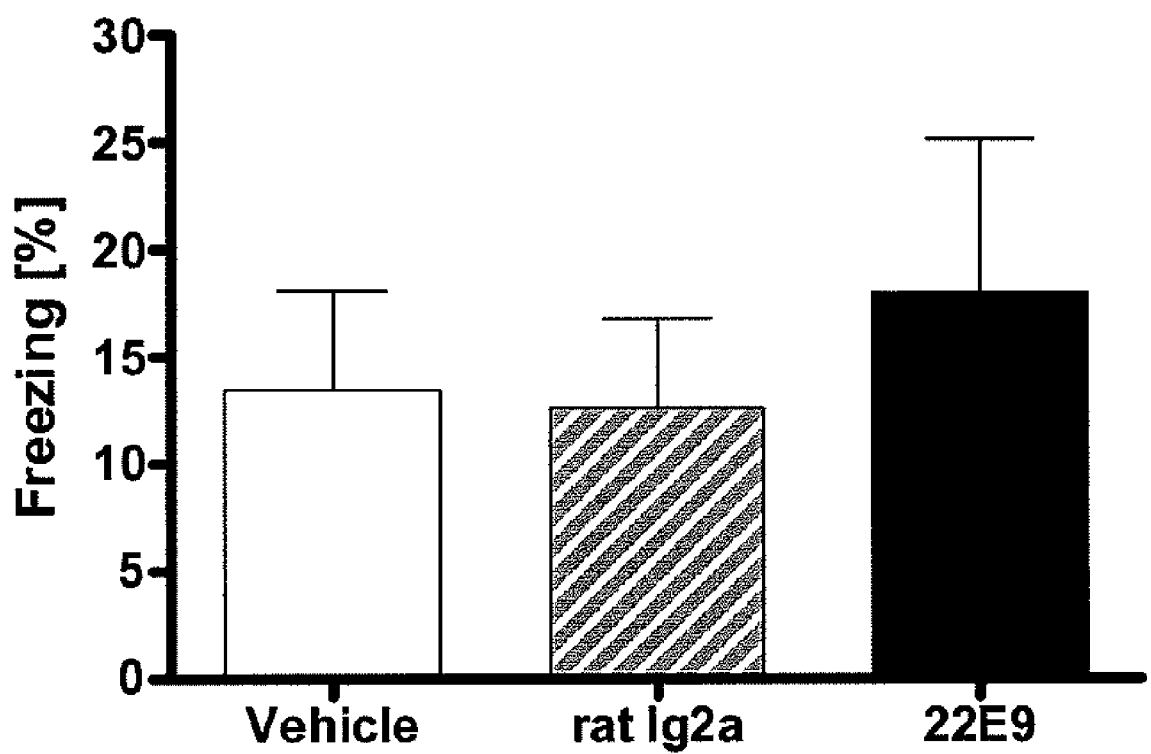
FIG. 4. Performance of anti-GM-CSF antibody 22E9 treated and control mice in the Contextual fear conditioning analysis beginning 51 days after treatment initiation. Context conditioned freezing response is shown for animals transferred to the training chamber 24 hours after initial training. Results are means+standard errors.

As used herein, "Alzheimer's disease" refers to senile dementia as diagnosed using commonly accepted criteria in the art, such as the criteria set forth by The National Institute of Neurological and Communicative Disorders and Stroke and the Alzheimer's disease and Related Disorders Association and/or the criteria as listed in the Diagnostic and Statistical Manual of Mental Disorders (DSM-IV-TR) published by the American Psychiatric Association. The Diagnostic and Statistical Manual of Mental Disorders (Fourth Edition, revised in 2000), also known as the DSM-IV-TR, outlines a detailed set of criteria for the diagnosis of Alzheimer's disease. For purposes of this application, the terms "Alzheimer's" and "Alzheimer's disease" and "AD" are used interchangeably.

"Vascular dementia" is a common form of dementia. The term "vascular dementia" refers to a group of syndromes relating to different vascular mechanisms. Various subtypes of vascular dementia have been described to date. The spectrum of disease includes (1) mild vascular cognitive impairment, (2) multi-infarct dementia, (3) vascular dementia due to a strategic single infarct, (4) vascular dementia due to lacunar lesions, (5) vascular dementia due to hemorrhagic lesions, (6) Binswanger disease, (7) subcortical vascular dementia, and (8) mixed dementia (combination of AD and vascular dementia). Vascular dementia is sometimes further classified as cortical or subcortical dementia. Vascular dementia can be diagnosed by clinical criteria, often in combination with brain imaging.

"Cerebral amyloid angiopathy" refers to a disorder characterized by deposition of amyloid within the walls of the cerebral arteries. Severe CAA is associated with vasculopathic changes, vessel rupture, and cerebral hemorrhage. CAA is a component of any disorder in which amyloid is deposited in the brain, e.g., Alzheimer's disease, and it is not associated with systemic amyloidosis.

In the current invention, a patient with "mild to moderate" dementia, or early-stage Alzheimer's disease can be identified using neurological testing and other clinical endpoints. For example, a subject with mild to moderate dementia, e.g., Alzheimer's disease, can be identified using the Mini-Mental State Examination (MMSE). Typically, a score of 16 to 26 (both inclusive) is indicative of mild to moderate Alzheimer's disease. Patients with advanced Alzheimer's disease can also be identified based on clinical parameters. Subjects with this form of Alzheimer's disease may no longer respond to therapy with acetylcholinesterase inhibitors, and may have a markedly reduced acetylcholine level.

As used herein, "Granulocyte Macrophage-Colony Stimulating Factor" (GM-CSF) refers to a small, naturally occurring glycoprotein with internal disulfide bonds having a molecular weight of approximately 23 kDa. In humans, it is encoded by a gene located within the cytokine cluster on human chromosome 5. The sequence of the human gene and protein are known. The protein has an N-terminal signal sequence, and a C-terminal receptor binding domain (Rasko and Gough In: The Cytokine Handbook, A. Thomson, et al, Academic Press, New York (1994) pages 349-369). Its three-dimensional structure is similar to that of the interleukins, although the amino acid sequences are not similar. GM-CSF is produced in response to a number of inflammatory mediators by mesenchymal cells present in the hemopoietic environment and at peripheral sites of inflammation. GM-CSF is able to stimulate the production of neutrophilic granulocytes, macrophages, and mixed granulocyte-macrophage colonies from bone marrow cells and can stimulate the formation of eosinophil colonies from fetal liver progenitor cells. GM-CSF can also stimulate some functional activities in mature granulocytes and macrophages.

The term "granulocyte macrophage-colony stimulating factor receptor" (GM-CSFR)" refers to a membrane bound receptor expressed on cells that transduces a signal when bound to granulocyte macrophage colony-stimulating factor (GM-CSF). GM-CSFR consists of a ligand-specific low-affinity binding chain (GM-CSFR alpha) and a second chain that is required for high-affinity binding and signal transduction. This second chain is shared by the ligand-specific alpha-chains for the interleukin 3 (IL-3) and IL-5 receptors and is therefore called beta common (beta c). The cytoplasmic region of GM-CSFR alpha consists of a membrane-proximal conserved region shared by the alpha 1 and alpha 2 isoforms and a C-terminal variable region that is divergent between alpha 1 and alpha 2. The cytoplasmic region of beta-c contains membrane proximal serine and acidic domains that are important for the proliferative response induced by GM-CSF.

The term "soluble granulocyte macrophage-colony stimulating factor receptor" (sGM-CSFR) refers to a non-membrane bound receptor that binds GM-CSF, but does not transduce a signal when bound to the ligand.

As used herein, a "peptide GM-CSF antagonist" refers to a peptide that interacts with GM-CSF, or its receptor, to reduce or block (either partially or completely) signal transduction that would otherwise result from the binding of GM-CSF to its cognate receptor expressed on cells. GM-CSF antagonists may act by reducing the amount of GM-CSF ligand available to bind the receptor (e.g., antibodies that once bound to GM-CSF increase the clearance rate of GM-CSF) or prevent the ligand from binding to its receptor either by binding to GM-CSF or the receptor (e.g., neutralizing antibodies). GM-CSF antagonists may also include other peptide inhibitors, which may include polypeptides, that bind GM-CSF or its receptor to partially or completely inhibit signaling. A peptide GM-CSF antagonist can be, e.g., an antibody; a natural or synthetic GM-CSF receptor ligand that antagonizes GM-CSF, or other polypeptides. An exemplary assay to detect GM-CSF antagonist activity is provided in Example 1. Typically, a peptide GM-CSF antagonist, such as a neutralizing antibody, has an $EC_{50}$ of 10 nM or less.

A "purified" GM-CSF antagonist as used herein refers to a GM-CSF antagonist that is substantially or essentially free from components that normally accompany it as found in its native state. For example, a GM-CSF antagonist such as an anti-GM-CSF antibody, that is purified from blood or plasma is substantially free of other blood or plasma components such as other immunoglobulin molecules. Purity and homogeneity are typically determined using analytical chemistry techniques such as polyacrylamide gel electrophoresis or high performance liquid chromatography. A protein that is the predominant species present in a preparation is substantially purified. Typically, "purified" means that the protein is at least 85% pure, more preferably at least 95% pure, and most preferably at least 99% pure relative to the components with which the protein naturally occurs.

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term antibody includes antibody fragments that retain binding specificity. For example, there are a number of well characterized antibody fragments. Thus, for example, pepsin digests an antibody C-terminal to the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include dimers such as $V_H$-$V_L$ dimers, $V_H$ dimers, or $V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. *Proc. Nat. Acad. Sci. USA,* 85:5879-5883, 1988). While the $V_H$ and $V_L$ are connected to each as a single polypeptide chain, the $V_H$ and $V_L$ domains associate non-covalently. Alternatively, the antibody can be another fragment, such as a disulfide-stabilized Fv (dsFv). Other fragments can also be generated, including using recombinant techniques. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). In some embodiments, antibodies include those that have been displayed on phage or generated by recombinant technology using vectors where the chains are secreted as soluble proteins, e.g., scFv, Fv, Fab, (Fab')$_2$ or generated by recombinant technology using vectors where the chains are secreted as soluble proteins. Antibodies for use in the invention can also include diantibodies and miniantibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called VHH domains. Antibodies for use in the current invention include single domain antibodies (dAbs) and nanobodies (see, e.g., Cortez-Retamozo, et al., *Cancer Res.* 64:2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene.

As used herein, the term "J-segment" refers to a subsequence of the encoded variable region comprising a C-terminal portion of a CDR3 and the FR4. An endogenous J-segment is encoded by an immunoglobulin J-gene.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.,* 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, *J. Mol. Biol.,* 262 (5), 732-745 (1996); and Martin et al, *Proc. Natl. Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "neutralizing antibody" refers to an antibody that binds to GM-CSF and prevents signaling by the GM-CSF receptor, or inhibits binding of GM-CSF to its receptor.

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule that confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci USA* 91: 969, 1994).

A "HUMANEERED™" antibody in the context of this invention refers to an engineered human antibody having a binding specificity of a reference antibody. A engineered human antibody for use in this invention has an immunoglobulin molecule that contains minimal sequence derived from a donor immunoglobulin. In some embodiments, the engineered human antibody may retain only the minimal essential binding specificity determinant from the CDR3 regions of a reference antibody. Typically, an engineered human antibody is engineered by joining a DNA sequence encoding a binding specificity determinant (BSD) from the CDR3 region of the heavy chain of the reference antibody to human $V_H$ segment sequence and a light chain CDR3BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for engineering human antibodies are provided in US patent application publication no. 20050255552 and US patent application publication no. 20060134098.

The term "human antibody" as used herein refers to an antibody that is substantially human, i.e., has FR regions, and often CDR regions, from a human immune system. Accordingly, the term includes humanized and humaneered antibodies as well as antibodies isolated from mice reconstituted with a human immune system and antibodies isolated from display libraries.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid.

The phrase "specifically (or selectively) binds" to an antibody or "specifically (or selectively) immunoreactive with," refers to a binding reaction where the antibody binds to the antigen of interest. In the context of this invention, the antibody typically binds to the antigen, e.g., GM-CSF, with an affinity of 500 nM or less, and has an affinity of 5000 nM or greater, for other antigens.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Nall. Acad. Sci. USA*

89:10915 (1989)) alignments (B) of 50, expectation (E) of 10, M=5, N=−4, and a comparison of both strands.

An indication that two polypeptides are substantially identical is that the first polypeptide is immunologically cross reactive with the antibodies raised against the second polypeptide. Thus, a polypeptide is typically substantially identical to a second polypeptide, e.g., where the two peptides differ only by conservative substitutions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables and substitution matrices such as BLOSUM providing functionally similar amino acids are well known in the art. Such conservatively modified variants are in addition to and do not exclude polymorphic variants, interspecies homologs, and alleles of the invention. Typical conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

I. Introduction

The invention relates to methods of administering a GM-CSF antagonist to a patient for the treatment of dementia, such as Alzheimer's disease, vascular dementia or CAA. Patient to be treated in accordance with the invention include patients having Alzheimer's disease, vascular dementia, or CAA; or a patient at risk for developing Alzheimer's disease, or vascular dementia. GM-CSF antagonists may include anti-GM-CSF antibodies, anti-GM-CSF receptor antibodies, or other inhibitors that prevent signaling that normally results from the binding of GM-CSF to its cognate receptor.

Antibodies, e.g., anti-GM-CSF or anti-GM-CSF receptor antibodies, suitable for use with the present invention may be monoclonal, polyclonal, chimeric, humanized, engineered human antibodies that contain only minimal sequence from a reference antibody, or human. Other GM-CSF antagonists suitable for use with the present invention may include naturally occurring or synthetic ligands (or fragments thereof) that compete with GM-CSF for binding to the receptor, but do not result in signaling when bound to the receptor. Additional non-limiting GM-CSF antagonists may include polypeptides, nucleic acids, small molecules and the like that either partially or completely block signaling that would naturally result from the binding of GM-CSF to its receptor in the absence of the GM-CSF antagonist.

In the context of the present specification, "beta-amyloid", "β-amyloid", "amyloid-beta", "amyloid-β" and "aβ" are used interchangeably to refer to beta amyloid peptides and include reference to various peptides, including $a\beta_{1-40}$, $a\beta_{1-42}$, $a\beta_{1-43}$, $a\beta_{1-44}$, and the like.

II. Patients

Alzheimer's Disease

Typical patients to be treated with the GM-CSF antagonist are those diagnosed with Alzheimer's disease or who have a familial disposition to Alzheimer's disease. For the purposes of this invention, an Alzheimer's patient is diagnosed according to accepted clinical criteria. There are two alternative diagnoses standards that are commonly employed to clinically diagnose Alzheimer's disease. The National Institute of Neurological and Communicative Disorders and Stroke and the Alzheimer's disease and Related Disorders Association (also referred to as NINCDS-ADRDA) established one set of commonly used diagnostic criteria for Alzheimer's disease, although other criteria can also be used (e.g., Dubois et al, *Lancet Neurol* 6 (8): 734-46, 2007). For the NINCDS-ADRDA criteria, the presence of cognitive impairment, and a suspected dementia syndrome is confirmed by neuropsychological testing for a clinical diagnosis of possible or probable AD. A definitive diagnosis is obtained by histopathological confirmation. As understood in the art, for the purposes of this invention, the terms "diagnosed with Alzheimer's disease" or a patient "having Alzheimer's disease" includes patients that have probable or possible Alzheimer's, as a definitive diagnosis under NINCDS-ADRDA diagnostic criteria is based on histopathologic evidence that is often obtained post-mortem. NINCDS-ADRDA diagnostic criteria are:

Definite Alzheimer's disease: The patient meets the criteria for probable Alzheimer's disease and has histopathologic evidence of AD via autopsy or biopsy.

Probable Alzheimer's disease: Dementia has been established by clinical and neuropsychological examination. Cognitive impairments is progressive and is present in two or more areas of cognition. The onset of the deficits has been between the ages of 40 and 90 years and there is an absence of other diseases capable of producing a dementia syndrome.

Possible Alzheimer's disease: There is a dementia syndrome with an atypical onset, presentation or progression; and without a known etiology; but no co-morbid diseases capable of producing dementia are believed to be in the origin of it.

Unlikely Alzheimer's disease: The patient presents a dementia syndrome with a sudden onset, focal neurologic signs, or seizures or gait disturbance early in the course of the illness.

Alzheimer's disease can also be diagnosed based on the criteria in the Diagnostic and Statistical Manual of Mental Disorders (DSM-IV-TR, 2000) published by the American Psychiatric Association. Briefly, the criteria for diagnosis of Alzheimer's disease under DSM-IV-TR include the development of multiple cognitive deficits manifested by both (1) memory impairment (impaired ability to learn new information or to recall previously learned information) and (2) one (or more) of the following cognitive disturbances: (a) aphasia (language disturbance), (b) apraxia (impaired ability to carry out motor activities despite intact motor function), (c) agnosia (failure to recognize or identify objects despite intact sensory function), (d) disturbance in executive functioning (i.e., planning, organizing, sequencing, abstracting). The cognitive deficits cause significant impairment in social or occupational functioning and represent a significant decline from a previous level of functioning. The course is characterized by gradual onset and continuing cognitive decline, and the all other specific causes of dementia are excluded by history, physical examination, and/or laboratory tests.

Other diagnostic procedures can also be used to diagnose Alzheimer's disease (see, e.g., Dubois et al., *Lancet Neurol*, Vol. 6:734-746, 2007). For example, such procedures include tests of episodic memory, e.g. delayed recall and double memory tests to differentiate between memory storage or encoding problems, which are indicative of Alzheimer's disease, and problems involving memory retrieval. Biochemical tests can also be used for diagnosis. For example, low amyloid $\beta_{(1-42)}$ concentrations, increased total tau concentrations, or increased phospho-tau concentrations or combinations of these three in a CSF sample, or other appropriate sample, from a patient is indicative of Alzheimer's disease. Neopterin levels in the serum of a patient, may also be evaluated to determine whether an elevated level, which is associated with Alzheimer's disease, is present (Leblhuber et al., *Clin. Chem. Lab. Med.* 37:429-431, 1999). Structural and metabolic evaluation can also be performed on the brain, e.g., PET scanning to identify diminished glucose metabolism in the bilateral temporoparietal regions and posterior cingulate. The presence of atrophy in the medial temporal lobe regions of the brain, including volume loss of hippocampi, entorhinal cortex, and amygdala, may also be determined using computed tomographic scanning (CT), and magnetic resonance imaging (MRI) (Leedom and Miller, "CT, MRI, and NMR Spectroscopy in Alzheimer's disease," Alzheimer's disease, Current Research in Early Diagnosis, Becker and Giacobini (eds.), pp. 297-313, 1990).

Genetic risk factors may also be evaluated to either aid in the diagnosis of Alzheimer's or to evaluate increased risk for developing Alzheimer's. In some embodiments, subjects that may have an increased risk for developing Alzheimer's disease can also be treated with a GM-CSF antagonist, e.g., an antibody as described herein.

In assessing genetic risk factors, subjects can be screened based on a number of biochemical and genetic markers. For example, genetic abnormality in a few families has been traced to chromosome 21 (St. George-Hyslop et al., Science 235:885-890, 1987). One genetic marker is, for example, the presence of mutations in the APP gene, particularly mutations at position 717 and positions 670 and 671, which are referred to as the Hardy and Swedish mutations, respectively. Other markers of risk are mutations in the presenilin genes, PS1 and PS2, the ApoE4 profile of a subject, family history of Alzheimer's disease, and the presence of risk factors such as hypercholesterolemia or atherosclerosis. Subjects with APP, PS1 or PS2 mutations are highly likely to develop Alzheimer's disease. Subjects having the E4 isoform of ApoE (ApoE4 isoform) have an increased risk of developing Alzheimer's disease.

Alzheimer's patients that can be treated in accordance with the methods of the invention include those with mild or moderate impairment as well as patients with more advanced impairment.

In some embodiments, a patient who has mild cognitive impairment (MCI) may be treated with a GM-CSF antagonist. MCI patients are at risk for development of Alzheimer's disease. MCI can be diagnosed and evaluated using any of the many objective tests or criteria well-known and accepted in the fields of psychology or psychiatry. For example, one criterion for the diagnosis of MCI is that the patient receives a clinical dementia rating of 0.5 as described, e.g., in Hughes et al., Brit. J. Psychiat. 140:566-572, 1982 and Morris, Neurology 43:2412-2414, 1993. In determining the clinical dementia rating, a patient is typically assessed and rated in each of six cognitive and behavioural categories: memory, orientation, judgment and problem solving, community affairs, home and hobbies, and personal care. The patient is assessed and rated in each of these areas and the overall rating, (0, 0.5, 1.0, 2.0 or 3.0) determined. A rating of 0 is considered normal. A rating of 1.0 is considered to correspond to mild dementia. A patient with cognitive impairment demonstrates impaired performance on a memory task test. Memory may be measured by such tests known in the art as the Wechsler Memory Scale or a pair-associated memory task. A patient is considered to exhibit impaired performance on such a test if the score is below the education and age-adjusted cutoff for that test.

In the current invention a patient diagnosed with Alzheimer's disease or at risk of developing Alzheimer's disease, e.g., has mild cognitive impairment, a family history of familial Alzheimer's, or a risk factor for developing Alzheimer's such as the Alzheimer's disease-associated ApoE subtype (ApoE4 subtype), may be treated with a GM-CSF antagonist as described herein.

Vascular Dementia

A GM-CSF antagonist, e.g., an anti-GM-CSF antibody, may also be used to treat a patient with vascular dementia. Vascular dementia is also known as ischemic vascular dementia or multi-infarct dementia. These terms refer to a group of syndromes caused by different mechanisms all resulting in vascular lesions in the brain. The main subtypes of vascular dementia described to date are vascular mild cognitive impairment, multi-infarct dementia, vascular dementia due to a strategic single infarct, vascular dementia due to hemorrhagic lesions, small vessel disease (which includes vascular dementia due to lacunar lesions and Binswanger disease), and Alzheimer's disease mixed with vascular dementia. Vascular lesions can be the result of diffuse cerebrovascular disease or focal lesions (or a combination of both, which is what is observed in the majority of cases). Vascular dementia is diagnosed based on clinical criteria, often in conjunction with neurological imaging to detect ischemic lesions. Mixed dementia is diagnosed when patients have evidence of Alzheimer's disease and cerebrovascular disease, either clinically or based on neuroimaging evidence of ischemic lesions.

In some embodiments, a patient who is at risk for vascular dementia, e.g., has transient ischemic episodes or has evidence of amyloid deposits in blood vessels of the brain, may be treated with a GM-CSF antagonist.

Cerebral Amyloid Angiopathy

In some embodiments, a patient treated with a GM-CSF antagonist, e.g., an anti-GM-CSF antibody, may have cerebral amyloid angiopathy (CAA), in which amyloid is deposited in the walls of the cerebral arteries. Although CAA has been recognized as one of the morphologic hallmarks of Alzheimer's disease, it is also often found in the brains of elderly patients who are otherwise neurologically healthy. While often asymptomatic, CAA may lead to dementia, intracranial hemorrhage, or transient neurologic events. Incranial hemorrhage (ICH) is the most recognized result of CAA. More than 40% of patients with ICH-related hemorrhage have some degree of dementia. In some cases, the cognitive changes can precede the ICH. Thus patients having cerebral amyloid angiopathy may have Alzheimer's disease, vascular dementia, or both, or may be at risk of developing Alzheimer's disease and/or vascular dementia.

A commonly used guideline for the diagnosis of CAA is the Boston Cerebral Amyloid Angiopathy Group guidelines. Often, CAA is accompanied by hemorrhage. The Boston Criteria for the diagnosis of CAA-related hemorrhage are based on a combination of clinical, radiologic, and pathologic data to differentiate lobar intracerebral hemorrhage into categories of possible, probable, or definite based on the likelihood of underlying cerebral amyloid angiopathy. As used herein in the context of this invention, a patient diagnosed with CAA may be diagnosed with possible or probable CAA and need not be definitively diagnosed, as definite CAA is typically determined postmortem.

Definite CAA: Full postmortem examination reveals lobar, cortical, or corticosubcortical hemorrhage and evidence of severe CAA.

Probable CAA with supporting pathological evidence: The clinical data and pathological tissue (evacuated hematoma or cortical biopsy specimen) demonstrate a hemorrhage with certain characteristics and some degree of vascular amyloid deposition.

Probable CAA: Clinical data and MRI findings (in the absence of a pathological specimen) demonstrate multiple hematomas (as described above) in a patient older than 60 years.

Possible CAA: This is considered if the patient is older than 60 years, and clinical and MRI data reveal a single lobar, cortical, or corticosubcortical hemorrhage without another cause, multiple hemorrhages with a possible but not a definite cause, or some hemorrhage in an atypical location.

In some embodiments, a patient that has Alzheimer's disease, vascular dementia, CAA, or is a candidate for developing Alzheimer's disease, vascular dementia, or both and is treated with a GM-CSF antagonist exhibits elevated GM-CSF levels, in comparison to normal healthy controls, in the cerebrospinal fluid or other sample, e.g., serum. Elevated levels of GM-CSF can be detected using many techniques commonly known in the art, e.g., an immunoassay.

III. GM-CSF Antagonists

As noted above, the invention provides methods for treating Alzheimer's disease, vascular dementia, or CAA by administering a GM-CSF antagonist to a patient suffering from the disease, or at risk of developing the disease. GM-CSF antagonists suitable for use in the invention selectively interfere with the induction of signaling by the GM-CSF receptor by causing a reduction in the binding of GM-CSF to the receptor. Such antagonists may include antibodies that bind the GM-CSF receptor, antibodies that bind to GM-CSF, GM-CSF analogs such as E21R, and other proteins or small molecules that compete for binding of GM-CSF to its receptor or inhibit signaling that normally results from the binding of the ligand to the receptor.

In many embodiments, the GM-CSF antagonist used in the invention is a polypeptide e.g., an anti-GM-CSF antibody, an anti-GM-CSF receptor antibody, a soluble GM-CSF receptor, or a modified GM-CSF polypeptide that competes for binding with GM-CSF to a receptor, but is inactive. Such proteins are often produced using recombinant expression technology. Such methods are widely are widely known in the art. General molecular biology methods, including expression methods, can be found, e.g., in instruction manuals, such as, Sambrook and Russell (2001) Molecular Cloning: A laboratory manual 3rd ed. Cold Spring Harbor Laboratory Press; Current Protocols in Molecular Biology (2006) John Wiley and Sons ISBN: 0-471-50338-X.

A variety of prokaryotic and/or eukaryotic based protein expression systems may be employed to produce a GM-CSF antagonist protein. Many such systems are widely available from commercial suppliers. These include both prokaryotic and eukaryotic expression systems.

GM-CSF Antibodies

In some embodiments, the GM-CSF antagonist is an antibody that binds to GM-CSF or an antibody that binds to the GM-CSF receptor α or β subunit. The antibodies can be raised against GM-CSF (or GM-CSF receptor) proteins, or fragments, or produced recombinantly. Antibodies to GM-CSF for use in the invention can be neutralizing or can be non-neutralizing antibodies that bind GM-CSF and increase the rate of in vivo clearance of GM-CSF such that the GM-CSF level in the circulation is reduced. Often, the GM-CSF antibody is a neutralizing antibody.

Methods of preparing polyclonal antibodies are known to the skilled artisan (e.g., Harlow & Lane, Antibodies, A Laboratory manual (1988); Methods in Immunology). Polyclonal antibodies can be raised in a mammal by one or more injections of an immunizing agent and, if desired, an adjuvant. The immunizing agent includes a GM-CSF or GM-CSF receptor protein, e.g., a human GM-CSF or GM-CSF receptor protein, or fragment thereof.

In some embodiment, a GM-CSF antibody for use in the invention is purified from human plasma. In such embodiments, the GM-CSF antibody is typically a polyclonal antibody that is isolated from other antibodies present in human plasma. Such an isolation procedure can be performed, e.g., using known techniques, such as affinity chromatography.

In some embodiments, the GM-CSF antagonist is a monoclonal antibody. Monoclonal antibodies may be prepared using hybridoma methods, such as those described by Kohler & Milstein, *Nature* 256:495 (1975). In a hybridoma method, a mouse, hamster, or other appropriate host animal, is typically immunized with an immunizing agent, such as human GM-CSF, to elicit lymphocytes that produce or are capable of producing antibodies that will specifically bind to the immunizing agent. Alternatively, the lymphocytes may be immunized in vitro. The immunizing agent preferably includes human GM-CSF protein, fragments thereof, or fusion protein thereof.

Human monoclonal antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., Nature 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

In some embodiments the anti-GM-CSF antibodies are chimeric or humanized monoclonal antibodies. As noted supra, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity.

An antibody that is employed in the invention can be in any format. For example, in some embodiments, the antibody can be a complete antibody including a constant region, e.g., a human constant region, or can be a fragment or derivative of a complete antibody, e.g., an Fd, a Fab, Fab', F(ab')$_2$, a scFv, an Fv fragment, or a single domain antibody, such as a nanobody or a camelid antibody. Such antibodies may additionally be recombinantly engineered by methods well known to persons of skill in the art. As noted above, such antibodies can be produced using known techniques.

In some embodiments of the invention, the antibody is additionally engineered to reduced immunogenicity, e.g., so that the antibody is suitable for repeat administration. Methods for generating antibodies with reduced immunogenicity include humanization/humaneering procedures and modification techniques such as de-immunization, in which an antibody is further engineered, e.g., in one or more framework regions, to remove T cell epitopes.

In some embodiments, the antibody is a humaneered antibody. A humaneered antibody is an engineered human antibody having a binding specificity of a reference antibody, obtained by joining a DNA sequence encoding a binding specificity determinant (BSD) from the CDR3 region of the heavy chain of the reference antibody to human VH segment sequence and a light chain CDR3BSD from the reference antibody to a human VL segment sequence. Methods for humaneering are provided in US patent application publication no. 20050255552 and US patent application publication no. 20060134098. Methods for signal-less secretion of antibody fragments from *E. coli* are described in US patent application 20070020685.

An antibody can further be de-immunized to remove one or more predicted T-cell epitopes from the V-region of an antibody. Such procedures are described, for example, in WO 00/34317.

In some embodiments, the variable region is comprised of human V-gene sequences. For example, a variable region sequence can have at least 80% identity, or at least 85% identity, at least 90% identity, at least 95% identity, at least 96% identity, at least 97% identity, at least 98% identity, or at least 99% identity, or greater, with a human germ-line V-gene sequence.

An antibody used in the invention can include a human constant region. The constant region of the light chain may be a human kappa or lambda constant region. The heavy chain constant region is often a gamma chain constant region, for example, a gamma-1, gamma-2, gamma-3, or gamma-4 constant region.

In some embodiments, e.g., where the antibody is a fragment, the antibody can be conjugated to another molecule, e.g., to provide an extended half-life in vivo such as a polyethylene glycol (pegylation) or serum albumin. Examples of PEGylation of antibody fragments are provided in Knight et al (2004) Platelets 15: 409 (for abciximab); Pedley et al (1994) Br. J. Cancer 70: 1126 (for an anti-CEA antibody) Chapman et al (1999) Nature Biotech. 17:780.

Antibody Specificity

An antibody for use in the invention binds to GM-CSF or GM-CSF receptor. Any number of techniques can be used to determine antibody binding specificity. See, e.g., Harlow & Lane, Antibodies, A Laboratory Manual (1988) for a description of immunoassay formats and conditions that can be used to determine specific immunoreactivity of an antibody.

An exemplary antibody suitable for use with the present invention is c19/2 (a human mouse chimeric anti-GM-CSF antibody). In some embodiments, a monoclonal antibody that competes for binding to the same epitope as c19/2, or that binds the same epitope as c19/2, is used. The ability of a particular antibody to recognize the same epitope as another antibody is typically determined by the ability of the first antibody to competitively inhibit binding of the second antibody to the antigen. Any of a number of competitive binding assays can be used to measure competition between two antibodies to the same antigen. For example, a sandwich ELISA assay can be used for this purpose. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Epitope Mapping

In some embodiments of the invention, an antibody is employed that competes with binding, or bind, to the same epitope as a known antibody, e.g., c19/2. Method of mapping epitopes are well known in the art. For example, one approach to the localization of functionally active regions of human granulocyte-macrophage colony-stimulating factor (hGM-CSF) is to map the epitopes recognized by neutralizing anti-hGM-CSF monoclonal antibodies. For example, the epitope to which c19/2 (which has the same variable regions as the neutralizing antibody LMM102) binds has been defined using proteolytic fragments obtained by enzymic digestion of bacterially synthesized hGM-CSF (Dempsey, et al., *Hybridoma* 9:545-558, 1990). RP-HPLC fractionation of a tryptic digest resulted in the identification of an immunoreactive “tryptic core” peptide containing 66 amino acids (52% of the protein). Further digestion of this “tryptic core” with *S. aureus* V8 protease produced a unique immunoreactive hGM-CSF product comprising two peptides, residues 86-93 and 112-127, linked by a disulfide bond between residues 88 and 121. The individual peptides, were not recognized by the antibody.

Determining Binding Affinity

In some embodiments, the antibodies suitable for use with the present invention have a high affinity binding for human GM-CSF or GM-CSF receptor. High affinity binding between an antibody and an antigen exists if the dissociation constant ($K_D$) of the antibody is <about 10 nM, typically <1 nM, and preferably <100 pM. In some embodiments, the antibody has a dissociation rate of about $10^{-4}$ per second or better.

A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al., (2007) *Mol. Immunol*. February; 44(5):916-25. (Epub 2006 May 11)).

Cell Proliferation Assay for Identifying Neutralizing Antibodies

In some embodiments, the GM-CSF antagonists are neutralizing antibodies to GM-CSF, or its receptor, which bind in a manner that interferes with the binding of GM-CSF. In some embodiments, an anti-GM-CSF antibody for use in the invention inhibits binding to the alpha subunit of the GM-CSF receptor. Such an antibody can, for example, bind to GM-CSF at the region where GM-CSF binds to the receptor and thereby inhibit binding.

Neutralizing antibodies and other GM-CSF antagonists may be identified using any number of assays that assess GM-CSF function. For example, cell-based assays for GM-CSF receptor signaling, such as assays which determine the rate of proliferation of a GM-CSF-dependent cell line in response to a limiting amount of GM-CSF, are conveniently used. The human TF-1 cell line is suitable for use in such an assay. See, Krinner et al., (2007) *Mol. Immunol*. In some embodiments, the neutralizing antibodies of the invention inhibit GM-CSF-stimulated TF-1 cell proliferation by at least 50% when a GM-CSF concentration is used which stimulates 90% maximal TF-1 cell proliferation. In other embodiments, the neutralizing antibodies inhibit GM-CSF stimulated proliferation by at least 90%. Thus, typically, a neutralizing antibody, or other GM-CSF antagonist for use in the invention, has an $EC_{50}$ of less than 10 nM (e.g., Table 1). Additional assays suitable for use in identifying neutralizing antibodies suitable for use with the present invention will be well known to persons of skill in the art.

Exemplary Antibodies

Antibodies for use in the invention are known in the art and can be produced using routine techniques. Exemplary antibodies are described. It is understood that the exemplary antibodies can be engineered in accordance with the procedures known in the art and summarized herein to produce antibody fragments, chimeras, and the like by either chemical or recombinant technology.

An exemplary chimeric antibody suitable for use as a GM-CSF antagonist is c19/2. The c19/2 antibody binds GM-CSF with a monovalent binding affinity of about 10 pM as determined by surface plasmon resonance analysis. The heavy and light chain variable region sequences of c19/2 are known (e.g., WO03/068920). The CDRs, as defined according to Kabat, are:

| | | |
|---|---|---|
| CDRH1 | DYNIH | (SEQ ID NO: 19) |
| CDRH2 | YIAPYSGGTGYNQEFKN | (SEQ ID NO: 20) |
| CDRH3 | RDRFPYYFDY | (SEQ ID NO: 5) |
| CDPW1 | KASQNVGSNVA | (SEQ ID NO: 21) |
| CDRL2 | SASYRSG | (SEQ ID NO: 22) |
| CDRL3 | QQFNRSPLT. | (SEQ ID NO: 23). |

In some embodiments, an antibody used in the invention competes for binding to, or binds to, the same epitope as c19/2. The GM-CSF epitope recognized by c19/2 has been identified as a product that has two peptides, residues 86-93 and residues 112-127, linked by a disulfide bond between residues 88 and 121. The c19/2 antibody inhibits the GM-CSF-dependent proliferation of a human TF-1 leukemia cell line with an $EC_{50}$ of 30 pM when the cells are stimulated with 0.5 ng/ml GM-CSF. In some embodiments, the antibody used in the invention binds to the same epitope as c19/2.

An antibody for administration, such as c19/2, can be additionally humaneered. For example, the c19/2 antibody can be further engineered to contain human V gene segments.

In some embodiments, a GM-CSF-binding antibody of the invention is generated where, an antibody that has a CDR from one of the $V_H$-regions of the invention shown in FIG. 1, is combined with one an antibody having a CDR of one of the V$_L$-regions shown in FIG. 1, and expressed in any of a number of formats in a suitable expression system. Thus the antibody may be expressed as a scFv, Fab, Fab' (containing an immunoglobulin hinge sequence), F(ab')$_2$, (formed by di-sulfide bond formation between the hinge sequences of two Fab' molecules), whole immunoglobulin or truncated immunoglobulin or as a fusion protein in a prokaryotic or eukaryotic host cell, either inside the host cell or by secretion. A methionine residue may optionally be present at the N-terminus, for example, in polypeptides produced in signal-less expression systems. Each of the V$_H$-regions described herein may be paired with each of the V$_L$ regions to generate an anti-GM-CSF antibody. Exemplary combinations of heavy and light chains are shown in the table in FIG. 1.

In some embodiment, the antibody VL region, e.g., VK#1, VK#2, VK#3, or VK#4 of FIG. 1, is combined with a human kappa constant region to form the complete light-chain. Further, in some embodiments, the VH region is combined a human gamma-1 constant regions. Any suitable gamma-1 allotype can be chose, such as the f-allotype. Thus, in some embodiments, the antibody is an IgG, e.g., having an f-allotype, that has a V$_H$ selected from VH#1, VH#2, VH#3, VH#4, or VH#5 (FIG. 1), and a V$_L$ selected from VK#1, VK#2, VK#3, or VK#4 (FIG. 1.)

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, the antibodies of the invention are in the form of a Fab' fragment. A full-length light chain is generated by fusion of a V$_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd' fragment generated by fusion of a V$_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. The Fab' antibodies of the invention may also be hybrid sequences, e.g., a hinge sequence may be from one immunoglobulin sub-class and the CH1 domain may be from a different sub-class.

Two other examples of neutralizing anti-GM-CSF antibody are the human E10 antibody and human G9 antibody described in Li et al., (2006) *PNAS*103(10):3557-3562. E10 and G9 are IgG class antibodies. E10 has an 870 pM binding affinity for GM-CSF and G9 has a 14 pM affinity for GM-CSF. Both antibodies are specific for binding to human GM-CSF and show strong neutralizing activity as assessed with a TF1 cell proliferation assay.

An additional exemplary neutralizing anti-GM-CSF antibody is the MT203 antibody described by Krinner et al., (*Mol Immunol.* 44:916-25, 2007; Epub 2006 May 112006). MT203 is an IgG1 class antibody that binds GM-CSF with picomolar affinity. The antibody shows potent inhibitory activity as assessed by TF-1 cell proliferation assay and its ability to block IL-8 production in U937 cells.

Additional antibodies suitable for use with the present invention will be known to persons of skill in the art.

GM-CSF antagonists that are anti-GM-CSF receptor antibodies can also be employed in the invention. Such GM-CSF antagonists include antibodies to the GM-CSF receptor alpha chain or beta chain. An anti-GM-CSF receptor antibody employed in the invention can be in any antibody format as explained above, e.g., intact, chimeric, monoclonal, polyclonal, antibody fragment, humanized, humaneered, and the like. Examples of anti-GM-CSF receptor antibodies, e.g., neutralizing, high-affinity antibodies, suitable for use in the invention are known (see, e.g., U.S. Pat. No. 5,747,032 and Nicola et al., *Blood* 82: 1724, 1993).

Non-Antibody GM-CSF Antagonists

Other proteins that may interfere with the productive interaction of GM-CSF with its receptor include mutant GM-CSF proteins and secreted proteins comprising at least part of the extracellular portion of one or both of the GM-CSF receptor chains that bind to GM-CSF and compete with binding to cell-surface receptor. For example, a soluble GM-CSF receptor antagonist can be prepared by fusing the coding region of the sGM-CSFRalpha with the CH2-CH3 regions of murine IgG2a. An exemplary soluble GM-CSF receptor is described by Raines et al. (1991) *Proc. Natl. Acad. Sci USA* 88: 8203. An example of a GM-CSFRalpha-Fc fusion protein is provided, e.g., in Brown et al (1995) Blood 85: 1488. In some embodiments, the Fc component of such a fusion can be engineered to modulate binding, e.g., to increase binding, to the Fc receptor.

Other GM-CSF antagonists include GM-CSF mutants. For example, GM-CSF having a mutation of amino acid residue 21 of GM-CSF to Arginine or Lysine (E21R or E21K) described by Hercus et al. *Proc. Natl. Acad. Sci USA* 91:5838, 1994 has been shown to have in vivo activity in preventing dissemination of GM-CSF-dependent leukemia cells in mouse xenograft models (Iversen et al. *Blood* 90:4910, 1997). As appreciated by one of skill in the art, such antagonists can include conservatively modified variants of GM-CSF that have substitutions, such as the substitution noted at amino acid residue 21, or GM-CSF variants that have, e.g., amino acid analogs to prolong half-life.

In some embodiments, the GM-CSF antagonist may be a peptide. For example, A GM-CSF peptide antagonist may be a peptide designed to structurally mimic the positions of specific residues on the B and C helices of human GM-CSF that are implicated in receptor binding and bioactivity (e.g., Monfardini et al., *J. Biol. Chem* 271:2966-2971, 1996).

In other embodiments, the GM-CSF antagonist is an "antibody mimetic" that targets and binds to the antigen in a manner similar to antibodies. Certain of these "antibody mimics" use non-immunoglobulin protein scaffolds as alternative protein frameworks for the variable regions of antibodies. For example, Ku et al. (*Proc. Natl. Acad. Sci. U.S.A.* 92(14):6552-6556 (1995)) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96(5):1898-1903 (1999)) disclose an antibody mimic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49(2):209-216 (2003)) describe a methodology for reducing antibodies into smaller peptidomimetics, they term "antibody-like binding peptidomimetics" (ABiP) which may also be useful as an alternative to antibodies.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody GM-CSF antagonists can also include such compounds.

III. Therapeutic Administration

The methods of the invention typically comprise administering a GM-CSF antagonist, (e.g., an anti-GM-CSF antibody) as a pharmaceutical composition to a patient suffering from one or more of Alzheimer's disease, vascular dementia, or CAA; or to a patient at risk of developing Alzheimer's and/or vascular dementia, in a therapeutically effective amount using a dosing regimen suitable for treatment of the disease.

In the present invention, a therapeutically effective amount is an amount that at least partially arrests symptoms and/or slows the progression or onset of Alzheimer's disease, vascular dementia, or CAA. For example, a therapeutically effective amount may slow deposition of amyloid, or reduce the size or number of amyloid plaques, in the brain and/or blood vessels. For example, the methods of the invention successfully treat a patient having Alzheimer's disease or vascular dementia by improving performance of memory task tests and/or slowing or preventing the rate of, or extent of, cognitive decline. Effectiveness may also be measured by assessing other parameters, such as biochemical markers or evaluating brain structure using CT scanning, MRI or PET scanning.

The composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy,* 21st Edition, Philadelphia, Pa. Lippincott Williams & Wilkins, 2005. For a brief review of methods for drug delivery, see, Langer, *Science* 249: 1527-1533 (1990).

The GM-CSF antagonist for use in the methods of the invention is provided in a solution suitable for injection into the patient such as a sterile isotonic aqueous solution for injection. The GM-CSF antagonist is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

Amounts that are administered that are effective will depend upon the severity of the disease and the general state of the patient's health, including other factors such as age, weight, gender, administration route, etc. Single or multiple administrations of the antagonist may be administered depending on the dosage and frequency as required and tolerated by the patient. In any event, the methods provide a sufficient quantity of GM-CSF antagonist in an amount to effectively treat the patient.

In some embodiments, the quantity of GM-CSF antagonist, e.g., anti-GM-CSF administered to the patient is an amount that results in improvement in performance on cognition tests used to measure cognitive function in dementia (see, e.g. Qaseem et al., Annals of Internal Medicine 148:370-378, 2008). The primary scales used to measure the domain of cognition deficits include the Alzheimer's Disease Assessment Scale (ADAS) cognitive subscale (ADAS-cog), non-cognitive subscale (ADAS-noncog) and total score (ADAS-tot); Mini-Mental State Examination (MMSE) or standardized MMSE; and the Severe Impairment Battery (SIB). For the domain of global assessment, the primary scale used include clinician-based impression of change (CIBIC) (with caregiver input [CIBIC-plus] and other modified versions). A patient receiving a therapeutically effective amount of a GM-CSF antagonist, e.g., an anti-GM-CSF antibody, may demonstrate improvement in perfoimance on any one of these tests, or alternative measures of cognitive function known in the art, or on multiple tests. Improvement is generally determined relative to a baseline value for cognitive function in the patient prior to treatment with a GM-CSF antagonist. In some embodiments, administration of an GM-CSF antagonist, e.g., an anti-GM-CSF antibody, to a patient results in maintained cognitive function where a patient does not exhibit a decline in cognitive function as measure by any a standard test.

In another embodiment of the invention, the GM-CSF antagonist used to treat a patient suffering from at least one of Alzheimer's disease, vascular dementia, or CAA; or who is at risk for developing Alzheimer's disease and/or vascular dementia, is provided in combination with one or more additional therapeutic agents for the treatment of the disease. Patients can receive the one or more additional therapeutic agents as concomitant therapy. Alternatively, patients may be treated sequentially, in any order, with the additional therapeutic agent(s) and GM-CSF antagonist. Examples of additional therapeutic agents include an anti-beta-amyloid antibody, e.g., bapineuzumab; an amyloid-beta (aβ) vaccine; cholesterol-lowering agents such as statins or inhibitors of acyl-coenzyme A:cholesterol acyltransferase (ACAT); non-steroidal anti-inflammatory drugs; an acetyl cholinesterase inhibitor, such as ARICEPT® (donepezil), EXELON® (rivastigmine), or RAZADYNE® (galantamine); an NMDA receptor antagonist, such as NAMENDA® (memantine); an antagonist to the receptor for advanced glycation endproducts (RAGE); a beta-secretase inhibitor; a gamma secretase inhibitor; IVIG, or a neuroprotective agent such as DIMEBON® (dimebolin).

A. Administration

In some embodiments, the GM-CSF antagonist is administered by injection or infusion through any suitable route including but not limited to intravenous, perispinal, subcutaneous, intramuscular, intranasal, perispinal, intrathecal, intraspinal or intraperitoneal routes. In an exemplary embodiment, the GM-CSF antagonist is diluted in a physiological saline solution for injection prior to administration to the patient. Such an antagonist is administered, for example, by intravenous infusion over a period of between 15 minutes and 2 hours. In still other embodiments, the administration procedure is via sub-cutaneous or intramuscular injection.

In some embodiments, the GM-CSF antagonist, e.g., an anti-GM-CSF antibody, is administered by a perispinal route. Perispinal administration involves anatomically localized delivery performed so as to place the therapeutic molecule directly in the vicinity of the spine at the time of initial administration. Perispinal administration is described, e.g., in U.S. Pat. No. 7,214,658 and in Tobinick & Gross, *J. Neuroinflammation* 5:2, 2008.

B. Dosing

The dose of GM-CSF antagonist is chosen in order to provide effective therapy for a patient that has been diagnosed with one or more of Alzheimer's disease, vascular dementia, or CAA, or is at risk for developing Alzheimer's disease or vascular dementia. The dose is typically in the range of about 0.1 mg/kg body weight to about 25 mg/kg body weight or in the range about 1 mg to about 2 g per patient. The dose is often in the range of about 1 to about 10 mg/kg or approximately about 50 mg to about 1000 mg/patient. The dose may be repeated at an appropriate frequency which may be in the range once per day to once every three months, depending on the pharmacokinetics of the antagonists (e.g. half-life of the antibody in the circulation) and the pharmacodynamic response (e.g. the duration of the therapeutic effect of the antibody). In some embodiments where the antagonist is an antibody or modified antibody fragment, the in vivo half-life of between about 7 and about 25 days and antibody dosing is repeated between once per week and once every 3 months. In other embodiments, the antibody is administered approximately once per month.

EXAMPLES

Example 1

Exemplary Humaneered Antibodies to GM-CSF

A panel of engineered Fab' molecules with the specificity of c19/2 were generated from epitope-focused human V-segment libraries as described in US patent application publication nos. 20060134098 and 20050255552. Full-length engineered V-regions from a Vh1-restricted library were selected that supported binding to recombinant human GM-CSF. The "full-length" V-kappa library was used as a base for construction of "cassette" libraries as described in US patent application publication no. 20060134098, in which only part of the murine c19/2 V-segment was initially replaced by a library of human sequences. Two types of cassettes were constructed. Cassettes for the V-kappa chains were made by bridge PCR with overlapping common sequences within the framework 2 region. In this way "front-end" and "middle" human cassette libraries were constructed for the human V-kappa III isotype. Human V-kappa III cassettes which supported binding to GM-CSF were identified by colony-lift binding assay and ranked according to affinity in ELISA. The V-kappa human "front-end" and "middle" cassettes were fused together by bridge PCR to reconstruct a fully human V-kappa region that supported GM-CSF binding activity. The engineered Fabs thus consist of engineered V-heavy and V-kappa regions that support binding to human GM-CSF.

Binding activity was determined by surface plasmon resonance (spr) analysis. Biotinylated GM-CSF was captured on a streptavidin-coated CM5 biosensor chip. Humaneered Fab fragments expressed from *E. coli* were diluted to a starting concentration of 30 nM in 10 mM HEPES, 150 mM NaCl, 0.1 mg/ml BSA and 0.005% P20 at pH 7.4. Each Fab was diluted 4 times using a 3-fold dilution series and each concentration was tested twice at 37 degrees C. to determine the binding kinetics with the different density antigen surfaces. The data from all three surfaces were fit globally to extract the dissociation constants.

Binding kinetics were analyzed by Biacore 3000 surface plasmon resonance (SPR). Recombinant human GM-CSF antigen was biotinylated and immobilized on a streptavidin CM5 sensor chip. Fab samples were diluted to a starting concentration of 3 nM and run in a 3 fold dilution series. Assays were run in 10 mM HEPES, 150 mM NaCl, 0.1 mg/mL BSA and 0.005% p20 at pH 7.4 and 37° C. Each concentration was tested twice. Fab' binding assays were run on two antigen density surfaces providing duplicate data sets. The mean affinity ($K_D$) for each of 6 various humaneered anti-GM-CSF Fab clones, calculated using a 1:1 Langmuir binding model, is shown in Table 1.

Fabs were tested for GM-CSF neutralization using a TF-1 cell proliferation assay. GM-CSF-dependent proliferation of human TF-1 cells was measured after incubation for 4 days with 0.5 ng/ml GM-CSF using a MTS assay (Cell titer 96, Promega) to determine viable cells. All Fabs inhibited cell proliferation in this assay indicating that these are neutralizing antibodies. There is a good correlation between relative affinities of the anti-GM-CSF Fabs and $EC_{50}$ in the cell-based assay. Anti-GM-CSF antibodies with monovalent affinities in the range 18 pM-104 pM demonstrate effective neutralization of GM-CSF in the cell-based assay.

Exemplary engineered anti-GM-CSF V region sequences are shown in FIG. 1.

TABLE 1

Affinity of anti-GM-CSF Fabs determined by surface plasmon resonance analysis in comparison with activity ($EC_{50}$) in a GM-CSF dependent TF-1 cell proliferation assay

| Fab | Monovalent binding affinity determined by SPR (pM) | $EC_{50}$(pM) in TF-1 cell proliferation assay |
|---|---|---|
| 94 | 18 | 165 |
| 104 | 19 | 239 |

TABLE 1-continued

Affinity of anti-GM-CSF Fabs determined by surface plasmon resonance analysis in comparison with activity ($EC_{50}$) in a GM-CSF dependent TF-1 cell proliferation assay

| Fab | Monovalent binding affinity determined by SPR (pM) | $EC_{50}$(pM) in TF-1 cell proliferation assay |
|---|---|---|
| 77 | 29 | 404 |
| 92 | 58 | 539 |
| 42 | 104 | 3200 |
| 44 | 81 | 7000 |

Example 2

Administration of a GM-CSF Antibody in a Mouse Model of Alzheimer's Disease

Transgenic mice over-expressing a mutant human amyloid precursor protein (hAPP) were used to evaluate the role of anti-mouse GM-CSF antibody 22E9 in an animal model of amyloid deposit-associated dementia. Mice over-expressing human APP(751) protein with three point mutations (K670M, N671L and V717I) under the control of the murine Thy-1 promoter were used (APP751-SL mice) on a C57BL/6xDBA genetic background. This line of transgenic mice shows a consistent age-dependent increase in accumulation of amyloid beta peptides 40 and 42 (Aβ40, Aβ42) in the brain. The mice develop plaques in the brain consisting of amyloid deposits, starting at approximately 4 to 6 months and show progressive deficits in learning and memory. By 8 months of age, the mice show a strongly developed amyloid pathology accompanied by inflammatory processes including prominent astrocytosis and microgliosis around mature neuritic amyloid plaques (Wang et al., *Vaccine* 25:3041, 2007; Hutter-Paier et al., *Neuron* 44:227, 2004).

For investigation of uptake of anti-GM-CSF antibody into the brain, 22E9 rat monoclonal anti-mouse GM-CSF antibody (R&D Systems) was administered by three different routes to female hAPP751-SL mice aged at least 10 months. Intracerebroventricular injection (i.c.); intranasal administration (i.n.); and intravenous injection (i.v.) were evaluated using a single dose of antibody (0.25 mg i.n., 0.25 mg iv. and 25 μg i.c). Mice were sacrificed 48 hours post inoculation and brain histology was carried out.

Male APP751-SL mice at an age of 8 months (±2 weeks) were randomly allocated to treatment groups (13 mice per group) and treated with rat anti-mouse GM-CSF antibody 22E9 (R&D Systems), or with rat IgG2a isotype control antibody, or with the vehicle phosphate buffered saline solution (PBS). Antibody or vehicle were administered intravenously twice weekly for 2 months.

Behavioral Tests
Morris Water Maze (MWM)

Forty four days after the initiation of treatment, mice were trained in the MWM spatial navigation task in which mice swim to locate a hidden platform using visual cues. The task is based on the principle that mice are motivated to escape from a water environment by the most direct route. The Morris Water Maze task was conducted in a black circular pool of diameter 100 cm filled with water at a temperature of 21±2° C., divided virtually into four sectors. A transparent platform was placed in the southwest quadrant 0.5 cm beneath the water surface. One day before the training session, animals were evaluated in a "pre-test" consisting of two 60 s trials, to ensure that the vision of each animal was normal. Only animals that completed this task successfully were included in the MWM testing. In the MWM task, mice were evaluated in three trials per day (each lasting 1 minute) for four consecutive days. Escape latency (time to find the hidden platform) and length of swimming path were measured. Differences between animals in treatment and control groups were analyzed by Student's t-tests to determine statistical significance.

Contextual Fear Conditioning Task (CFC)

The fear conditioning task was conducted in an automated box provided by TSE-Systems, Germany. Mice were trained and tested on 2 consecutive days starting at Day 51 of the study. Training consisted of placing a subject into the test chamber and allowing exploration for 2 min. Thereafter, an auditory cue [2 Hz; conditional stimulus (CS)] was presented for 15 sec. An electric shock [1.5 mAmp; unconditioned stimulus (US)] was given for the final 2 sec of the CS. This procedure was repeated, and mice were removed from the chamber. Twenty hours after training, mice were returned to the training chambers (context conditioned response), and freezing behavior was recorded automatically. At the end of the 5 min contextual testing, mice were returned to their home cage. Approximately 1 h later, freezing was recorded in a novel environment and in response to the cue. In the CFC task, duration of freezing behavior of each subject, expressed as a percentage of each part of the test, was recorded.

Histology

Animals were sacrificed 48 hours after a single administration of antibody or on day 54 of the therapeutic study. Brains were rapidly removed and right hemispheres were fixed in 4% Paraformaldehyde/PBS (pH 7.4) for one hour at room temperature, transferred to a 15% sucrose PBS solution for 24 hours to ensure cryoprotection, and stored at −80° C. Brain hemispheres from 6 animals in each treatment group were used to provide sagittal sections (10 μm thick) using a cryotome for the determination of plaque load visualized by a ThioflavinS staining or with an amyloid specific antibody (anti-hAPP clone 6E10 (Signet 1: 5000)) and fluorescent Cy3-labeled secondary antibody (Jackson Immunoresearch). The estimation of plaque size, area and number were determined using computer-aided quantification. Uptake of 22E9 antibody into the brain was visualized using an anti-rat IgG antibody labeled with HistoGreen (Linaris®).

Results

Uptake of 22E9 into the brain was first evaluated by three different routes of administration in hAPP751-SL mice: intracerebroventricular injection (i.c.); intranasal administration (i.n.); and intravenous injection (i.v.). A single dose of antibody was administered (0.25 mg i.n., 0.25 mg iv. and 25 μg i.c) to mice aged at least 10 months and brain histology was carried out 48 hours post-administration. Staining with anti-rat IgG-specific antibody demonstrated that i.c. treatment led to clear uptake of 22E9 with particularly intense labeling of regions associated with hippocampal and thalamic plaques. Both i.v. and i.n. treatment also led to significant antibody uptake into the brain where accumulation was detected around microglia, particularly associated with hippocampal and thalamic amyloid plaques (see FIG. 2). This provides alternative routes of administration of anti-GM-CSF antibodies allowing uptake into the brain in the context of amyloid-related disease without the need for direct stereotactic injection into the cerebroventricular space.

Eight-month old male transgenic APP751-SL mice were then treated by twice weekly i.v. administration with 22E9 anti-GM-CSF antibody at 10 mg/kg or with isotype-matched (rat IgG2a) control antibody at the same dose level or vehicle alone (PBS). From Day 44 after the initiation of treatment (after 13 doses of antibody), mice were evaluated in the Morris Water Maze. Mice treated with anti-GM-CSF antibody 22E9 showed improved learning ability in this task over the 4 days of evaluation compared with vehicle treated or isotype control-treated mice (see FIG. 3). The difference in swimming path length between anti-GM-CSF treated and isotype control treated mice achieved statistical significance by Day 4 of the test. The escape latency also showed a trend to improvement by Day 4 of the test in the anti-GM-CSF treated mice compared with the group receiving the control antibody but the difference did not achieve statistical significance.

At Day 51 of the study (after 15 doses), mice were evaluated in a contextual fear study in which the freezing behavior in response to a training chamber and auditory cue was evaluated. Anti-GM-CSF treated mice showed a tendency to freeze for a longer time when placed in the training chamber compared with vehicle or isotype-control treated mice (see FIG. 4). No differences in response to auditory cues were observed in this experiment.

These data indicate that anti-GM-CSF treatment led to reduction in the learning deficit in mice transgenic for mutant human APP using two tests for visuo-spatial learning ability (the Morris Water Maze and Contextual fear conditioning).

Figure 5:
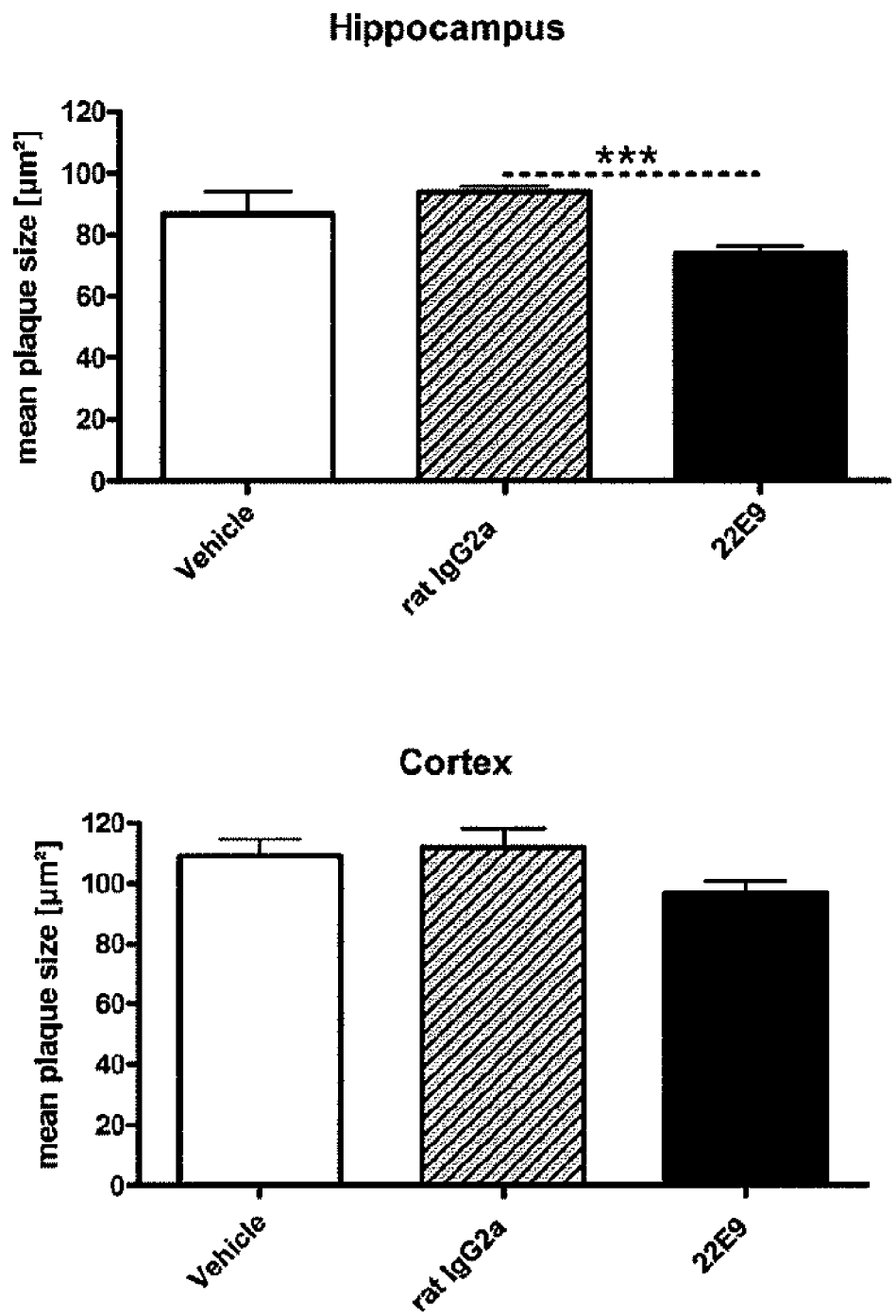
FIG. 5. Mean size of amyloid plaques in the brains of mice treated with anti-GM-CSF antibody 22E9 or control-treated mice. Mean plaque size (+standard error) from 6 mice in each group was determined by staining with 6E10 antibody to human amyloid. Data were analyzed by one-way Analysis of variance (ANOVA).

Histological analysis was carried out on regions of the brain of mice at the end of the therapeutic study (Day 54). Immunohistochemistry using antibody 6E10 specific for human amyloid indicated the presence of amyloid plaques in all evaluated mice but the mean plaque size was significantly reduced in the hippocampus of mice treated with 22E9 antibody compared with isotype-control treated mice (see FIG. 5). Plaque size also appeared to be reduced in the cortex of anti-GM-CSF treated mice compared with control animals. Plaque number was also quantified but showed no significant differences between the treated and control animals in this study at the time point that was analyzed. Staining for ThioS-positive did not reveal significant differences between the mature, condensed neuritic plaques of treated and control mice at Day 54 in this experiment.

The effects of administration of an anti-GM-CSF antibody in another transgenic AD mouse model were also investigated, the Tg2576 model. This Alzheimer's disease mouse model was generated using mutant human APP gene 695 amino acid isoform with a double mutation (K670N and M671L). Administration of anti-GM-CSF directly into the brains of Tg2576 mice decreased soluble $a\beta_{1-42}$ production and suppressed microglial activity in the mice (Maczak et al., *Hum. Molec. Genet.* 18:3876-3893, 2009).

The above examples are provided by way of illustration only and not by way of limitation. Those of skill in the art will readily recognize a variety of noncritical parameters that could be changed or modified to yield essentially similar results.

All publications, patent applications, accession numbers, and other references cited in this specification are herein incorporated by reference as if each individual publication or patent application were specifically and individually indicated to be incorporated by reference.

What is claimed is:

1. A method for treating a patient suffering from Alzheimer's disease, the method comprising administering a recombinant neutralizing anti-GM-CSF antibody to the patient, wherein the anti-GM-CSF antibody has a heavy chain variable ($V_H$) region and a light chain variable ($V_L$) region and is provided in a therapeutically effective amount.

2. The method of claim 1, wherein the anti-GM-CSF antibody is provided in a therapeutically effective amount to treat cognitive decline.

3. The method of claim 1, wherein the anti-GM-CSF antibody is administered intravenously or subcutaneously.

4. The method of claim 3, wherein the patient has mild to moderate Alzheimer's disease.

5. The method of claim 1, wherein the patient has both Alzheimer's disease and vascular dementia.

6. The method of claim 1, wherein the patient has both Alzheimer's disease and cerebral amyloid angiopathy.

7. The method of claim 1, wherein the patient has a family history of familial Alzheimer's disease.

8. The method of claim 1, further comprising administering an anti-amyloidβ antibody or administering an amyloidβ vaccine.

9. The method of claim 1, further comprising administering an acetylcholinesterase inhibitor or an NMDA receptor antagonist.

10. The method of claim 1, wherein the patient has elevated levels of GM-CSF in the cerebrospinal fluid or serum.

11. The method of claim 1, wherein the anti-GM-CSF antibody is a polyclonal antibody.

12. The method of claim 1, wherein the anti-GM-CSF antibody is a monoclonal antibody.

13. The method of claim 1, wherein the anti-GM-CSF antibody is an antibody fragment that is a Fab, a Fab', a F(ab')$_2$, a scFv, or a dAB.

14. The method of claim 13, wherein the antibody fragment is conjugated to polyethylene glycol.

15. The method of claim 1, wherein the anti-GM-CSF antibody has an affinity ranging from about 5 pM to about 50 pM.

16. The method of claim 1, wherein the anti-GM-CSF antibody is a chimeric antibody.

17. The method of claim 1, wherein the anti-GM-CSF antibody is a human antibody.

18. The method of claim 1, wherein the anti-GM-CSF antibody comprises a human variable region.

19. The method of claim 1, wherein the anti-GM-CSF antibody comprises a human light chain constant region and/or a human heavy chain constant region.

20. The method of claim 19, wherein the human heavy chain constant region is a gamma chain.

21. The method of claim 1, wherein the anti-GM-CSF antibody binds to the same epitope as chimeric 19/2.

22. The method of claim 1, wherein the anti-GM-CSF antibody comprises the $V_H$ region CDR3 and $V_L$ region CDR3 of chimeric 19/2; or wherein the anti-GM-CSF antibody comprises the $V_H$ region and $V_L$ region CDR1, CDR2, and CDR3 of chimeric 19/2.

23. The method of claim 1, wherein the anti-GM-CSF antibody comprises the CDR1, CDR2, and CDR3 of a $V_H$ region of SEQ ID NO8, SEQ ID NO:10, SEQ ID NO:11, SEQ ID NO:12, or SEQ ID NO:13; and the CDR1, CDR2, and CDR3 of a $V_L$ region of SEQ ID NO:15, SEQ ID NO:16, SEQ ID NO:17, or SEQ ID NO:18.

24. The method of claim 23, wherein the V-segment sequence has a $V_H$ V segment sequence.

25. The method of claim 23, wherein the $V_H$ has the sequence of SEQ ID NO8, SEQ ID NO:10, SEQ ID NO:11, SEQ ID NO:12, or SEQ ID NO:13.

26. The method of claim 23, wherein the $V_L$ region has the sequence of SEQ ID NO:15, SEQ ID NO:16, SEQ ID NO:17, or SEQ ID NO:18.

27. The method of claim 1 wherein the anti-GM-CSF antibody has a $V_H$ region sequence of SEQ ID NO8, SEQ ID NO:10, SEQ ID NO:11, SEQ ID NO:12, or SEQ ID NO:13 and a $V_L$ region sequence of SEQ ID NO:15, SEQ ID NO:16, SEQ ID NO:17, or SEQ ID NO:18.

28. A method for treating a patient suffering from Alzheimer's disease who has an elevated level of GM-CSF in the cerebrospinal fluid or serum, the method comprising administering a therapeutically effective amount of a neutralizing anti-GM-CSF antibody intravenously or subcutaneously, wherein the anti-GM-CSF antibody comprises a human engineered Fab' with the binding specificity of chimeric 19/2 and has an affinity ranging from about 5 to about 50 pM.

29. A method for treating a patient suffering from Alzheimer's disease, the method comprising administering a therapeutically effective amount of a neutralizing anti-GM-CSF antibody intravenously or subcutaneously to the patient.

30. The method of claim 29, further comprising administering an antibody to amyloidβ, an amyloidβ vaccine, an acetylcholinesterase inhibitor, an NMDA antagonist, or IVIG.

* * * * *

SEQUENCE LISTING

```
<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region CDR3 binding specificity determinant

<400> SEQUENCE: 1

Arg Gln Arg Phe Pro Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region CDR3 binding specificity determinant

<400> SEQUENCE: 2

Arg Asp Arg Phe Pro Tyr
1               5

<210> SEQ ID NO 3
<211> LENGTH: 15
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody J
      segment JH4
```

```
<400> SEQUENCE: 3

Tyr Phe Asp Tyr Trp Gly Gln Gly Thr Leu Val Thr Val Ser Ser
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region CDR3

<400> SEQUENCE: 4

Arg Gln Arg Phe Pro Tyr Tyr Phe Asp Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region CDR3, chimeric antibody c19/2 CDRH3

<400> SEQUENCE: 5

Arg Asp Arg Phe Pro Tyr Tyr Phe Asp Tyr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-L region CDR3
<220> FEATURE:
<221> NAME/KEY: VARIANT
<222> LOCATION: (5)...(5)
<223> OTHER INFORMATION: Xaa = Lys or Arg

<400> SEQUENCE: 6

Gln Gln Phe Asn Xaa Ser Pro Leu Thr
1               5

<210> SEQ ID NO 7
<211> LENGTH: 98
<212> TYPE: PRT
<213> ORGANISM: Homo sapiens
<220> FEATURE:
<223> OTHER INFORMATION: human germ line VH1 1-02

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80
```

-continued

Met Glu Leu Ser Arg Leu Arg Ser Asp Asp Thr Ala Val Tyr Tyr Cys
                    85                  90                  95

Ala Arg

<210> SEQ ID NO 8
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region VH#1

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                    85                  90                  95

Val Arg Arg Asp Arg Phe Pro Tyr Tyr Phe Asp Tyr Trp Gly Gln Gly
                100                 105                 110

Thr Leu Val Thr Val Ser Ser
        115

<210> SEQ ID NO 9
<211> LENGTH: 98
<212> TYPE: PRT
<213> ORGANISM: Homo sapiens
<220> FEATURE:
<223> OTHER INFORMATION: human germ line VH1 1-03

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg

<210> SEQ ID NO 10
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region VH#2

```
<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Arg Phe Pro Tyr Tyr Phe Asp Tyr Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region VH#3

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gln Arg Phe Pro Tyr Tyr Phe Asp Tyr Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region VH#4

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30
```

```
Tyr Ile His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
         50                  55                  60

Gln Gly Arg Val Ala Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Arg Gln Arg Phe Pro Tyr Tyr Phe Asp Tyr Trp Gly Gln Gly
                100                 105                 110

Thr Leu Val Thr Val Ser Ser
            115

<210> SEQ ID NO 13
<211> LENGTH: 119
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region VH#5

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Asn Tyr
             20                  25                  30

Tyr Ile His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
         50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Arg Gln Arg Phe Pro Tyr Tyr Phe Asp Tyr Trp Gly Gln Gly
                100                 105                 110

Thr Leu Val Thr Val Ser Ser
            115

<210> SEQ ID NO 14
<211> LENGTH: 96
<212> TYPE: PRT
<213> ORGANISM: Homo sapiens
<220> FEATURE:
<223> OTHER INFORMATION: human germ line VKIII A27 V-segment

<400> SEQUENCE: 14

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 15
<211> LENGTH: 107
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-L region VK#1

<400> SEQUENCE: 15

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
                20                  25                  30

Val Ala Trp Tyr Gln Gln Lys Pro Gly Gln Ala Pro Arg Val Leu Ile
            35                  40                  45

Tyr Ser Thr Ser Arg Ala Thr Gly Ile Thr Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                85                  90                  95

Thr Phe Gly Gly Gly Thr Lys Val Glu Ile Lys
            100                 105
```

<210> SEQ ID NO 16
<211> LENGTH: 107
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-H region VK#2

<400> SEQUENCE: 16

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
                20                  25                  30

Val Ala Trp Tyr Gln Gln Lys Pro Gly Gln Ala Pro Arg Val Leu Ile
            35                  40                  45

Tyr Ser Thr Ser Arg Ala Thr Gly Ile Thr Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys
            100                 105
```

<210> SEQ ID NO 17
<211> LENGTH: 107
<212> TYPE: PRT
<213> ORGANISM: Artificial Sequence
<220> FEATURE:
<223> OTHER INFORMATION: synthetic anti-granulocyte-macrophage
colony-stimulating factor (anti-GM-CSF) antibody
V-H region VK#3

<400> SEQUENCE: 17

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
            20                  25                  30

Leu Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                85                  90                  95

Thr Phe Gly Gly Gly Thr Lys Val Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: synthetic anti-granulocyte-macrophage
colony-stimulating factor (anti-GM-CSF) antibody
V-H region VK#4

<400> SEQUENCE: 18

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
            20                  25                  30

Leu Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys
            100                 105

<210> SEQ ID NO 19
<211> LENGTH: 5
<212> TYPE: PRT
<213> ORGANISM: Artificial Sequence
<220> FEATURE:
<223> OTHER INFORMATION: synthetic anti-granulocyte-macrophage
colony-stimulating factor (anti-GM-CSF) chimeric
antibody c19/2 CDRH1

<400> SEQUENCE: 19

Asp Tyr Asn Ile His
1               5

```
<210> SEQ ID NO 20
<211> LENGTH: 17
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) chimeric
      antibody c19/2 CDRH2

<400> SEQUENCE: 20

Tyr Ile Ala Pro Tyr Ser Gly Gly Thr Gly Tyr Asn Gln Glu Phe Lys
1               5                   10                  15
Asn

<210> SEQ ID NO 21
<211> LENGTH: 11
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) chimeric
      antibody c19/2 CDRL1

<400> SEQUENCE: 21

Lys Ala Ser Gln Asn Val Gly Ser Asn Val Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) chimeric
      antibody c19/2 CDRL2

<400> SEQUENCE: 22

Ser Ala Ser Tyr Arg Ser Gly
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) chimeric
      antibody c19/2 CDRL3

<400> SEQUENCE: 23

Gln Gln Phe Asn Arg Ser Pro Leu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic anti-granulocyte-macrophage
      colony-stimulating factor (anti-GM-CSF) antibody
      V-L region CDR3

<400> SEQUENCE: 24

Gln Gln Phe Asn Lys Ser Pro Leu Thr
1               5
```